US012601463B2

(12) United States Patent      (10) Patent No.:    US 12,601,463 B2

Chase et al.            (45) Date of Patent:      Apr. 14, 2026

(54) DEVICES, SYSTEMS, AND METHODS FOR SURGICAL LIGHT SPOT SIZE ADJUSTMENT

(71) Applicant: Stryker Corporation, Kalamazoo, MI (US)

(72) Inventors: David Patrick Chase, Southlake, TX (US); Gianni Boccoleri, Lantana, TX (US)

(73) Assignee: Stryker Corporation, Portage, MI (US)

( * ) Notice: Subject to any disclaimer, the term of this patent is extended or adjusted under 35 U.S.C. 154(b) by 224 days.

(21) Appl. No.: 18/356,835

(22) Filed: Jul. 21, 2023

(65) Prior Publication Data

US 2024/0027055 A1     Jan. 25, 2024

Related U.S. Application Data

(60) Provisional application No. 63/369,214, filed on Jul. 22, 2022.

(51) Int. Cl.
    *F21V 14/06*       (2006.01)
    *A61B 90/35*       (2016.01)
             (Continued)

(52) U.S. Cl.
    CPC .............. *F21V 14/06* (2013.01); *A61B 90/35* (2016.02); *F21V 5/007* (2013.01); *F21V 17/02* (2013.01);
             (Continued)

(58) Field of Classification Search
    CPC ................................ F21V 14/06; F21V 5/007
    See application file for complete search history.

(56) References Cited

U.S. PATENT DOCUMENTS 5,068,768 A * 11/1991 Kobayashi ............ F21S 41/635
                                  362/268
6,866,401 B2 * 3/2005 Sommers .............. F21V 14/065
                                  362/240

(Continued)

FOREIGN PATENT DOCUMENTS

WO      2014/036509 A1     3/2014

OTHER PUBLICATIONS

International Search Report and Written Opinion mailed Nov. 8, 2023, directed to International Application No. PCT/US2023/070728; 9 pages.

(Continued)

*Primary Examiner* — Tracie Y Green
*Assistant Examiner* — Michael Chiang
(74) *Attorney, Agent, or Firm* — Morrison & Foerster LLP

(57) ABSTRACT

Systems, devices, and methods are described herein for adjusting the spot size of light provided from a surgical light by translating a focus panel relative to a plurality of light emitters. The focus panel can be mounted to the housing of the surgical light such that the focus panel can translate relative to the housing in an axial direction toward and away from the plurality of light emitters. The focus panel can engage with one or more tracks that are movably mounted relative to the housing and controlled via at least one actuator. The actuator(s) can be configured to translate the focus panel towards or away from the plurality of light emitters to adjust the spot size of light provided by the surgical light via the engagement between the focus panel and the one or more tracks.

19 Claims, 16 Drawing Sheets

(51) Int. Cl.

| | |
|---|---|
| *F21V 5/00* | (2018.01) |
| *F21V 17/02* | (2006.01) |
| *F21V 21/30* | (2006.01) |
| *F21W 131/205* | (2006.01) |

(52) U.S. Cl.

CPC ....... *F21V 21/30* (2013.01); *F21W 2131/205* (2013.01)

(56) References Cited

U.S. PATENT DOCUMENTS

| | | | | |
|---|---|---|---|---|
| 10,203,094 | B2 * | 2/2019 | Hsu | F21V 5/007 |
| 10,247,392 | B2 * | 4/2019 | Huang | F21V 19/02 |
| 12,116,132 | B2 * | 10/2024 | Jha | B64D 11/00 |
| 12,140,292 | B2 * | 11/2024 | Chen | F21V 14/06 |
| 2010/0265706 | A1 * | 10/2010 | Hsing Chen | F21V 14/06 |
| | | | | 362/285 |
| 2012/0121244 | A1 | 5/2012 | Stavely | |
| 2012/0127710 | A1 * | 5/2012 | Jurik | F21V 11/16 |
| | | | | 362/235 |
| 2014/0049967 | A1 * | 2/2014 | Zhou | F21K 9/23 |
| | | | | 362/287 |
| 2017/0090115 | A1 * | 3/2017 | Jurik | F21V 14/006 |
| 2017/0219186 | A1 * | 8/2017 | Enno | F21V 5/007 |
| 2017/0299152 | A1 * | 10/2017 | Teder | F21L 4/02 |
| 2019/0041028 | A1 * | 2/2019 | Bremerich | F21V 14/08 |
| 2019/0093859 | A1 * | 3/2019 | Peard | G02B 6/0008 |

OTHER PUBLICATIONS

International Preliminary Report on Patentability dated Jan. 28, 2025, directed to International Application No. PCT/ US2023/ 070728; 5 pages.

* cited by examiner

DEVICES, SYSTEMS, AND METHODS FOR SURGICAL LIGHT SPOT SIZE ADJUSTMENT

CROSS-REFERENCE TO RELATED APPLICATIONS

This application claims the benefit of U.S. Provisional Application No. 63/369,214, filed Jul. 22, 2022, the entire contents of which are hereby incorporated by reference herein.

FIELD

The present disclosure relates generally to surgical lighting, and more specifically to spot size adjustment for surgical lighting.

BACKGROUND

Surgical lights can be used in operating rooms to illuminate a desired area of a patient undergoing a surgical procedure. During a surgical procedure, it can be useful to adjust the size of the area being illuminated (often referred to as the "spot size"). For example, a specific procedure may involve the surgeon viewing a relatively larger area of a patient for some time followed by viewing a smaller area afterwards. Thus, the surgeon may desire relative widely dispersed illumination light when viewing the larger area, followed by more concentrated illumination light when viewing the smaller area.

To adjust spot size, conventional surgical lights can include one or more optical controls. For instance, a surgical light can include a fixed optical system that adjusts spot size by turning on or off individual light emitters of the surgical light. However, turning off some light emitters to adjust spot size can reduce the amount of illumination provided at the target or require excess light emitters in the surgical light to maintain the same level of illumination. Incorporating surplus light emitters in a surgical light can increase both the size and cost of the surgical light, as well as add extra weight to the surgical light.

SUMMARY

According to an aspect, a surgical light includes a focus panel that is translatable relative to a plurality of light emitters to adjust the spot size of the surgical light. The focus panel is configured for engaging one or more tracks that are movably mounted relative to a housing of the surgical light, such that as the tracks move, the focus panel is translated toward or away from the plurality of light emitters, thereby adjusting the spot size of the surgical light. The focus panel can include a plurality of lenses aligned with the plurality of light emitters, with the lenses configured to control the spot size of light by redirecting and/or collimating the light that passes through them. The effect the lenses have on the light that passes through them varies based on the distance between the light emitters and the focus panel. For instance, when the focus panel and light emitters move closer to one another, the lenses of the focus panel redirect the light over a larger area thereby increasing the spot size of light emitted from the surgical light. Movement of the focus panel away from the light emitters has the opposite effect. Accordingly, the spot size can be adjusted without changing the number of light emitters for illumination.

In one or more examples, a surgical light comprises: a housing, a plurality of light emitters mounted to the housing, a focus panel assembly mounted to the housing such that the focus panel assembly is translatable relative to the housing, wherein the focus panel assembly is translatable in an axial direction toward and away from the plurality of light emitters, at least one track movably mounted to the housing and engaged by at least one tab of the focus panel assembly, and at least one actuator for moving the at least one track such that the at least one tab of the focus panel assembly travels along the at least one track, thereby axially translating the focus panel assembly toward or away from the plurality of light emitters for adjusting a spot size of light provided by the surgical light at a target.

Optionally, the housing comprises a plurality of alignment pins and the focus panel assembly is mounted to the housing such that the plurality of alignment pins prevent the focus panel assembly from rotating relative to the housing.

Optionally, the at least one track is located centrally with respect to the focus panel assembly.

Optionally, a ring is rotatably mounted to the housing and the ring comprises the at least one track.

Optionally, the at least one track is located at a periphery of the focus panel assembly.

Optionally, a ring peripherally located relative to the focus panel assembly comprises the at least one track.

Optionally, the at least one track comprises a plurality of tracks.

Optionally, the at least one actuator comprises a single actuator that moves the plurality of tracks.

Optionally, the at least one actuator comprises a plurality of actuators that move the plurality of tracks.

Optionally, the at least one track comprises at least one ramped portion for driving the focus panel assembly in the axial direction and at least one flat portion for retaining the focus panel assembly in an axial position.

Optionally, the at least one track comprises a ramped portion for driving the focus panel assembly in the axial direction.

Optionally, a sliding panel comprises the at least one track and a rack, the sliding panel movably mounted relative to the housing and engaged by the at least one tab of the focus panel assembly, and the at least one actuator comprises a pinion for driving the rack.

Optionally, the at least one actuator comprises a ring-shaped rack that drives a rod to which the pinion is mounted.

Optionally, the ring-shaped rack drives a plurality of rods that drive a plurality of tracks.

Optionally, the plurality of light emitters are arranged in a plurality of subgroups and the focus panel assembly comprises a plurality of subgroups of lenses, each subgroup of lenses being able to independently align to a corresponding subgroup of light emitters.

Optionally, the surgical light further comprises a controller that is communicably coupled to the at least one actuator, wherein the controller is configured to cause the at least one actuator to move the at least one track in response to receiving a command.

Optionally, the command corresponds to a predefined focus setting and the at least one track is moved by a predefined amount associated with the predefined focus setting.

In one or more examples, a method for adjusting a spot size of light provided by a surgical light at a target comprises: receiving a command at a controller of the surgical light to adjust the spot size of light, and in response to receiving the command, moving at least one track movably mounted to a housing of the surgical light by at least one actuator such that at least one tab of a focus panel assembly of the surgical light travels along the at least one track, thereby axially translating the focus panel assembly in an axial direction toward or away from a plurality of light emitters mounted to the housing, wherein the focus panel assembly is mounted to the housing such that the focus panel assembly is translatable relative to the housing.

Optionally, the housing comprises a plurality of alignment pins and the focus panel assembly is mounted to the housing such that the plurality of alignment pins prevent the focus panel assembly from rotating relative to the housing.

Optionally, the command corresponds to a predefined focus setting and the at least one track is moved by a predefined amount associated with the predefined focus setting.

Optionally, the at least one track is located centrally with respect to the focus panel assembly.

Optionally, a ring is rotatably mounted to the housing and the ring comprises the at least one track.

Optionally, the at least one track is located at a periphery of the focus panel assembly.

Optionally, a ring peripherally located relative to the focus panel assembly comprises the at least one track.

Optionally, the at least one track comprises a plurality of tracks.

Optionally, moving the plurality of tracks comprises moving, by a single actuator of the surgical light, the plurality of tracks.

Optionally, moving the plurality of tracks comprises moving, by a plurality of actuators of the surgical light, the plurality of tracks.

Optionally, the at least one track comprises at least one ramped portion and at least one flat portion, and moving the at least one track comprises: driving the focus panel assembly in the axial direction via the at least one ramped portion, and retaining the focus panel assembly in at least one axial position via the at least one flat portion.

Optionally, the at least one track comprises a ramped portion, and moving the at least one track comprises driving the focus panel assembly in the axial direction via the ramped portion.

Optionally, a sliding panel comprises the at least one track and a rack and the at least one actuator comprises a pinion for driving the rack.

Optionally, the at least one actuator comprises a ring-shaped rack that drives a rod to which the pinion is mounted.

Optionally, the ring-shaped rack drives a plurality of rods that drive a plurality of tracks.

Optionally, the plurality of light emitters are arranged in a plurality of subgroups and the focus panel assembly comprises a plurality of subgroups of lenses, each subgroup of lenses being able to independently align to a corresponding subgroup of light emitters.

It will be appreciated that any of the variations, aspects, features, and options described in view of the systems apply equally to the methods and vice versa. It will also be clear that any one or more of the above variations, aspects, features, and options can be combined.

BRIEF DESCRIPTION OF THE FIGURES

The invention will now be described, by way of example only, with reference to the accompanying drawings, in which.

DETAILED DESCRIPTION

Figure 1:
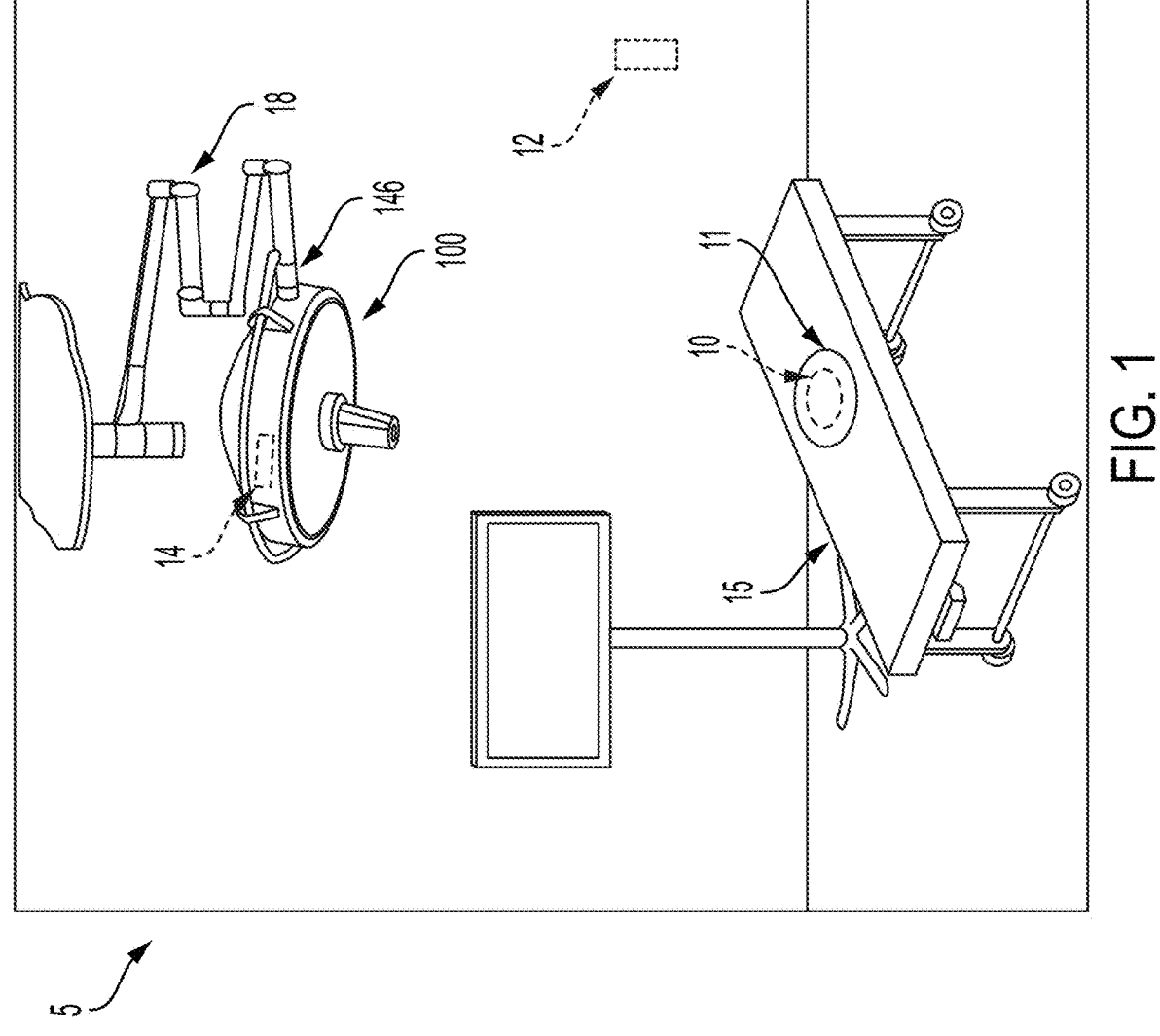
FIG. 1 shows an exemplary operating room, according to one or more examples of the disclosure.

In the following description of the various examples, reference is made to the accompanying drawings, in which are shown, by way of illustration, specific examples that can be practiced. The description is presented to enable one of ordinary skill in the art to make and use the invention and is provided in the context of a patent application and its requirements. Various modifications to the described examples will be readily apparent to those persons skilled in the art and the generic principles herein may be applied to other examples. Thus, the present invention is not intended to be limited to the examples shown but is to be accorded the widest scope consistent with the principles and features described herein.

Systems, devices, and methods are described herein for adjusting the spot size of light provided from a surgical light by translating a focus panel relative to a plurality of light emitters. The focus panel for example includes a plurality of lenses that are aligned with the plurality of light emitters. Translation of the focus panel moves the lenses toward or away from the light emitters, thereby adjusting the spot size at the target. The focus panel engages with one or more movable tracks that are controlled via at least one actuator and are configured to translate the focus panel towards or away from the light emitters based on the movement of the tracks. If the track(s) move in a first direction, for example, the focus panel moves towards the light emitters, thereby increasing the spot size of the light emitted from the surgical light. If the track(s) move in a second direction that is opposite the first direction, however, the focus panel moves away from the light emitters, thereby decreasing the spot size of light emitted from the surgical light.

The lenses of the focus panel can adjust the spot size by redirecting and/or collimating the light that passes through them, with the effect on the light varying based on the distance between the light emitters and the focus panel. At relatively short distances, the lenses of the focus panel can redirect the light from the light emitters over a larger area. As this distance increases, the lenses can redirect the light into a narrower beam of light that is concentrated on a relatively smaller area.

By utilizing a translatable focus panel, spot size can be adjusted without changing the number of light emitters used for illumination, which efficiently utilizes the light emitters of the surgical light. Relative to conventional surgical lights that rely on different combinations of emitters to adjust spot size, the surgical lights described herein can be lower weight and less costly because excess light emitters are not required.

The surgical light includes one or more movable tracks that engage with the focus panel to translate the focus panel. The one or more tracks can each include a ramped portion that engages with a tab of the focus panel such that as the track and ramped portion move, the tab of the focus panel follows the ramped portion. As the tab of the focus panel follows the ramped portion, the focus panel translates toward or away from the light emitters depending on the direction of movement of the movable tracks. The focus panel can include a number of tabs arranged around the central and/or peripheral perimeter of the focus panel to help maintain parallelism of the focus panel relative to the light emitters as the focus panel translates.

The tracks can be located on a central area of the housing and can engage with tabs that are centrally located on the focus panel. Additionally or alternatively, the tracks can be located on a peripheral area of the housing and can engage with tabs that are peripherally located on the focus panel. The tracks may be located on a rotating mechanism such as a rotating ring that is centrally or peripherally located, such that as the ring rotates the tracks move. Optionally, the tracks may be located on a slider mechanism that is movably mounted to the housing, such that as the slider mechanism moves the tracks move. As discussed above, the movement of the tracks can cause the focus panel to follow the track such that the focus panel moves toward or away from the light emitters. The tracks can also include flat portions that can retain the tabs of the focus panel in a given axial position. Thus, the tracks can translate the focus panel along an axis toward or away from the light emitters in order to adjust the spot size of light provided by the surgical light, and can also retain the focus panel in a given position along that axis in order to maintain the desired spot size.

To move the tracks, the surgical light incorporates one or more actuators. The actuators can include a pinion that engages with a rack, such that the rack translates the rotational movement of the pinion into movement of the rack. The movement of the rack can cause the tracks to move, thereby translating the focus panel. Optionally, the rack can be circular, and the tracks can be configured to move based on the rotational movement of the circular rack. The surgical light can include a single actuator configured to move a plurality of tracks, or a plurality of actuators. Each of the plurality of actuators may be individually engaged with a track, with the plurality of actuators synchronized such that they move the tracks in unison.

The surgical light can include a number of alignment pins. The alignment pins can ensure the focus panel remains aligned with the light emitters. Each alignment pin can be fixedly attached to or part of the housing of the surgical light and engaged with the focus panel such that the focus panel is only permitted to translate toward or away from the light emitters. The engagement between the focus panel and the alignment pins can ensure that the lenses of the focus panel remain aligned with the light emitters as the focus panel translates and can prevent the focus panel from rotating relative to the housing. The surgical light can include a number of alignment pins arranged around the surgical light, such that the alignment pins also serve to ensure the focus panel remains parallel as the focus panel translates toward or away from the light emitters. The surgical light can be configured such that the focus panel is not prevented from rotating relative to the housing.

As used herein, the singular forms "a," "an," and "the" used in the following description are intended to include the plural forms as well unless the context clearly indicates otherwise. It is to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present invention include process steps and instructions described herein in the form of a method. It should be noted that the process steps and instructions of the present invention could be embodied in software, firmware, or hardware, and, when embodied in software, they could be downloaded to reside on, and be operated from, different platforms used by a variety of operating systems. Unless specifically stated otherwise as apparent from the following discussion, it is appreciated that, throughout the description, discussions utilizing terms such as "processing," "computing," "calculating," "determining," "displaying," or the like refer to the action and processes of a computer system, or similar electronic computing device, that manipulates and transforms data represented as physical (electronic) quantities within the computer system memories or registers or other such information storage, transmission, or display devices.

The present disclosure can relate to a networked device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 shows an exemplary operating room 5, according to one or more examples of the disclosure. The operating room 5 can include a table 15 for supporting a patient and one or more surgical lights 100 for illuminating a target area of the patient. The one or more surgical lights 100 can be mounted to one or more boom structures 18, such as via a mounting interface 146. The boom structure(s) 18 can enable the one or more surgical lights 100 to be repositioned as desired. As will be described further below, the surgical light 100 is configured to provide different spot sizes of illumination at the target area without changing the number of light emitters that are emitting light. FIG. 1 illustrates two exemplary spot sizes 10 and 11. However, it should be understood that the surgical light 100 can be configured to provide any desired number of spot sizes. The spot size of the illumination provided by the surgical light 100 can be selected by a user, such as via a user interface 14 on the surgical light 100, or user interface 12 located remotely from the surgical light 100.

Figure 2:
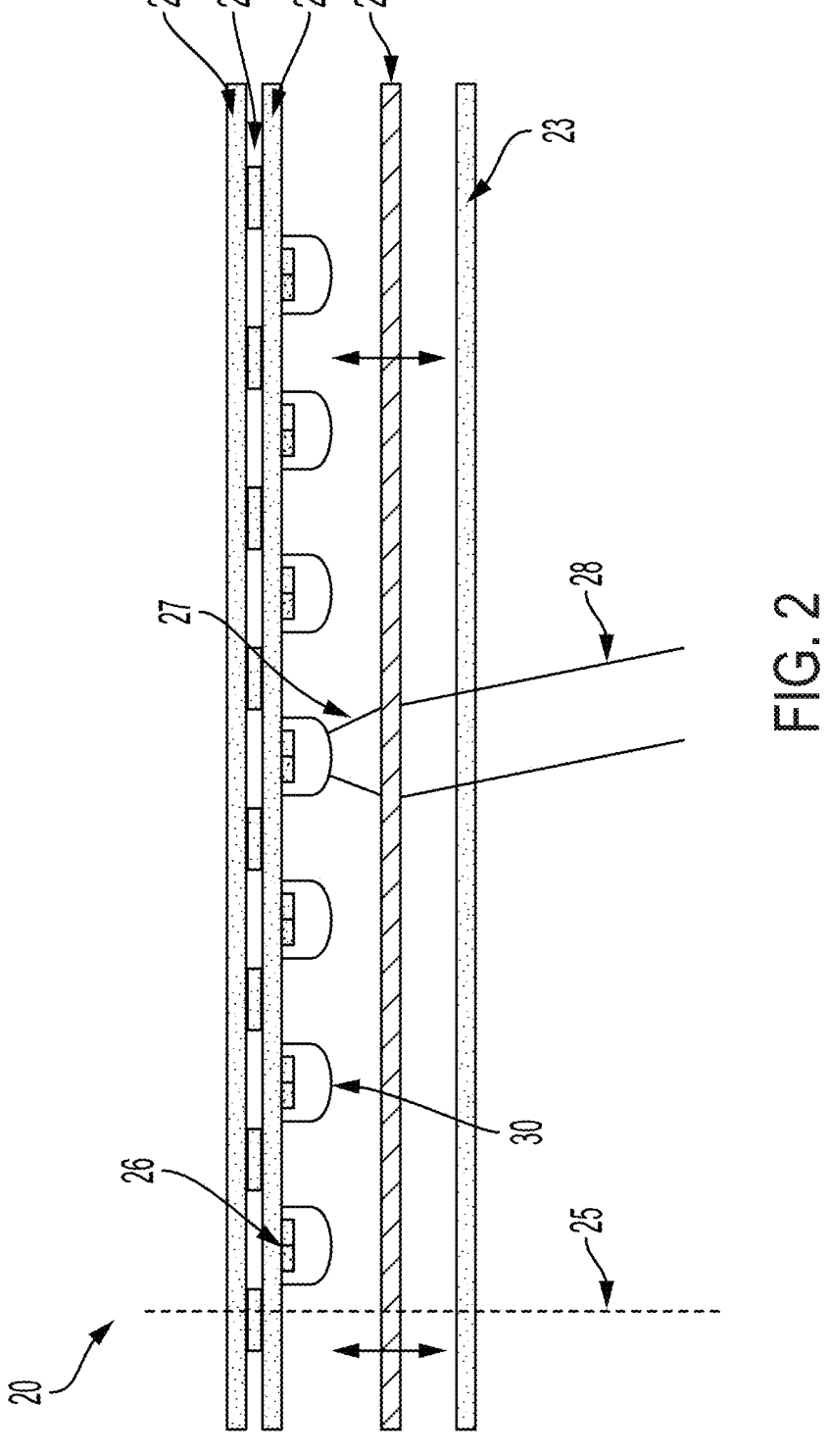
FIG. 2 shows a cross sectional view of an exemplary surgical light with a focus mechanism, according to one or more examples of the disclosure.

FIG. 2 shows a cross sectional view of an exemplary surgical light 20 that includes a translatable focus panel 22 for adjusting the spot size of light provided by the surgical light 20. The surgical light 20 can be used, for example, in an operating room, (e.g., as surgical light 100 shown in FIG. 1). The focus panel 22 permits a user to easily and efficiently adjust the spot size of light provided by the surgical light 20 without changing the number of light emitters that are emitting light.

The spot size of light emitted from light emitters 26 of the surgical light 20 is adjusted by changing the distance between the focus panel 22 and the light emitters 26. The effect of the focus panel 22 on the light 27 varies based on the distance between the light emitters 26 and the focus panel 22 along the axis 25. The spot size increases as the focus panel 22 moves toward the light emitters 26 and decreases as the focus panel 22 moves away from the light emitters 26. Accordingly, the spot size of the light emitted from the light emitters 26 can be controlled based on the axial location of the focus panel 22. The range of axial travel of the focus panel 22 can correspond with the desired range of spot sizes of light emitted from the surgical light 20. An exemplary range of travel is 9 mm. Optionally, the range of travel of the focus panel 22 can be less than 9 mm, such as 4 mm or 5 mm. Optionally, the range of travel of the focus panel 22 can be greater than 9 mm, such as 22 mm or 25 mm.

As shown in FIG. 2, the surgical light 20 includes a housing 24. The housing 24 can be a rigid or semi-rigid material. The housing 24 can be formed of a thermally conductive material such as aluminum that permits the housing 24 to act as a heatsink. The light emitters 26 can be fixedly mounted relative to the housing 24. For example, the light emitters 26 can be mounted to one or more printed circuit boards 28, and the one or more printed circuit boards 28 can be mounted to the housing 24 either directly or, for example, via one or more thermal pads 29. Heat generated by the surgical light 20, such as by a controller and/or the one or more printed circuit boards 28 of the surgical light 20, can be dissipated via the thermal pads 29 and the housing 24. For example, heat can be dissipated via the thermal pads 29 and then via the housing 24. The surgical light 20 can also include a transparent face panel 23 that covers the light emitting side of the surgical light 20. Optionally, the light emitters 26 can each include one or more light emitting diodes (LEDs). Optionally, the light emitters 26 can be organic light emitting diodes (OLEDs), organic electroluminescent diodes, superluminescent diodes (SLDs), or other alternate solid state light sources.

The surgical light 20 can include an optical element 30 positioned in front of each light emitter 26. The optical element 30 can include, for example, single or dual stage optical element(s) that perform pre-focusing of light radiation (e.g., by reducing the light source radiation angle) and/or mix the spectral power distribution of the radiated light. The focus panel 22 can include a number of lenses (not shown in figure) that are aligned with each light emitter 26 and optical element 30. After light passes through the optical element 30, the light 27 encounters the lenses of the focus panel 22, which may collimate and/or redirect the light 27 to adjust the spot size. As shown in FIG. 2, after encountering the focus panel 22, the light 27 was redirected into the redirected light 28.

When translating the focus panel 22 along the axis 25, alignment between the focus panel 22 and the light emitters 26 may be maintained so that the light emitted from the light emitters 26 is uniformly directed by the optical elements of the focus panel 22. As such, the surgical light 20 may be configured such that the focus panel 22 translates only in the direction along the axis 25, and is fixed from translating in any other directions. Alternatively, the surgical light 20 can be configured such that the focus panel 22 is permitted to translate along the axis 25 but is not fixed from translating in one or more other directions.

Figure 3:
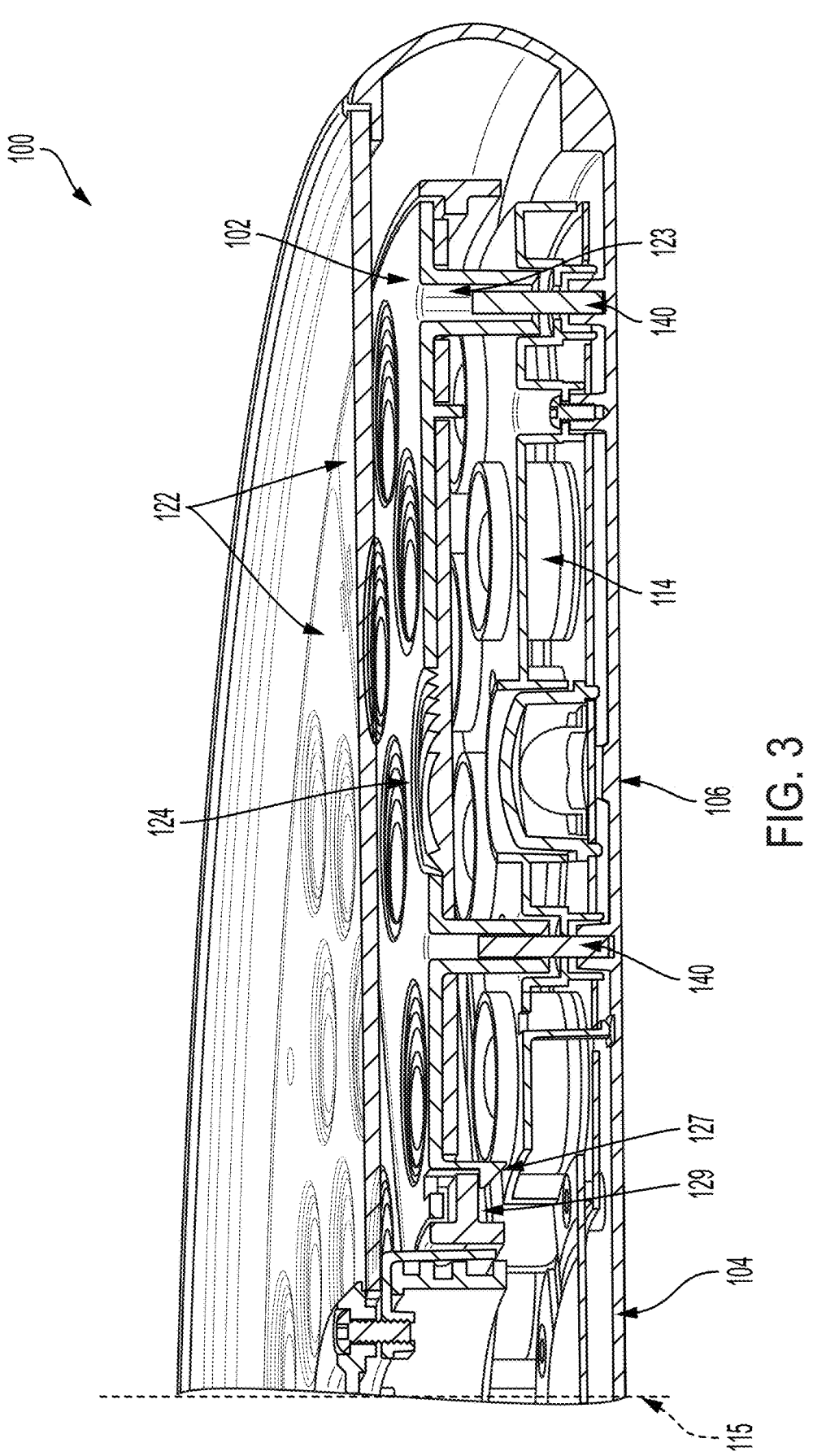
FIG. 3 shows a side cut away view of an exemplary surgical light with a focus mechanism, according to one or more examples of the disclosure.

One configuration for maintaining the alignment of the components of a surgical light with a translatable focus panel is shown in FIG. 3, which illustrates a side cut away view of a surgical light 100. The surgical light 100 can be configured as described above to include a focus panel 102 that can translate relative to light emitters 106 along axis 115.

As shown, the focus panel 102 includes a number of interface elements 123 that are engaged with a number of alignment pins 140. The alignment pins 140 protrude orthogonally from the housing 104 and can be part of the housing 104 or can be fixedly mounted to the housing 104, such that the alignment pins 140 remain fixed relative to the housing. For example, the alignment pins 140 can be attached to the housing 104 via press fitting. The engagement between the interface elements 123 of the focus panel 102 and the alignment pins 140 can ensure that the focus panel 102 moves only along the axis 115 toward or away from the light emitters 106. The alignment pins 140 and interface elements 123 can be configured with a clearance between them such that the focus panel 102 can translate along the axis 115 toward and away from the light emitters 106, as will be described further below.

The focus panel 102 includes a number of lenses 124 arranged within a number of lens panels 122. The lenses 124 of the focus panel 102 can redirect and/or collimate the light received from the light emitters 106 based on the distance between the lenses 124 and the light emitters 106 along the axis 115. For example, when the light emitters 106 and the lenses 124 of the focus panel 102 are moved closer to one another, the lenses 124 of the focus panel 102 can redirect the light emitted from the light emitters 106 over a larger area, thereby increasing the spot size of light emitted from the surgical light 100. Movement of the focus panel 102 away from the light emitters 106 has the opposite effect. Accordingly, the surgical light 100 can adjust the spot size of light provided from the light emitters 106 based on the lenses 124 of the focus panel 102 and the translation of the focus panel 102 without changing the number of light emitters 106 used to illuminate one spot size versus another.

As shown in FIG. 3, each lens 124 of the focus panel 102 is aligned with a light emitter 106 and an optical element 114. As discussed above, the engagement between the alignment pins 140 and the interface elements 123 can ensure that the focus panel 102 is fixed in all directions except along the axis 115. Thus, as the focus panel 102 moves toward or away from the light emitters 106, the alignment between the lenses 124 of the focus panel 102 and the light emitters 106 and the optical elements 114 remains constant. The alignment pins 140 can maintain the alignment of the components of the surgical light 100 while permitting the focus panel 102 to translate in order to adjust the spot size of light provided by the light emitters 106.

Figure 4:
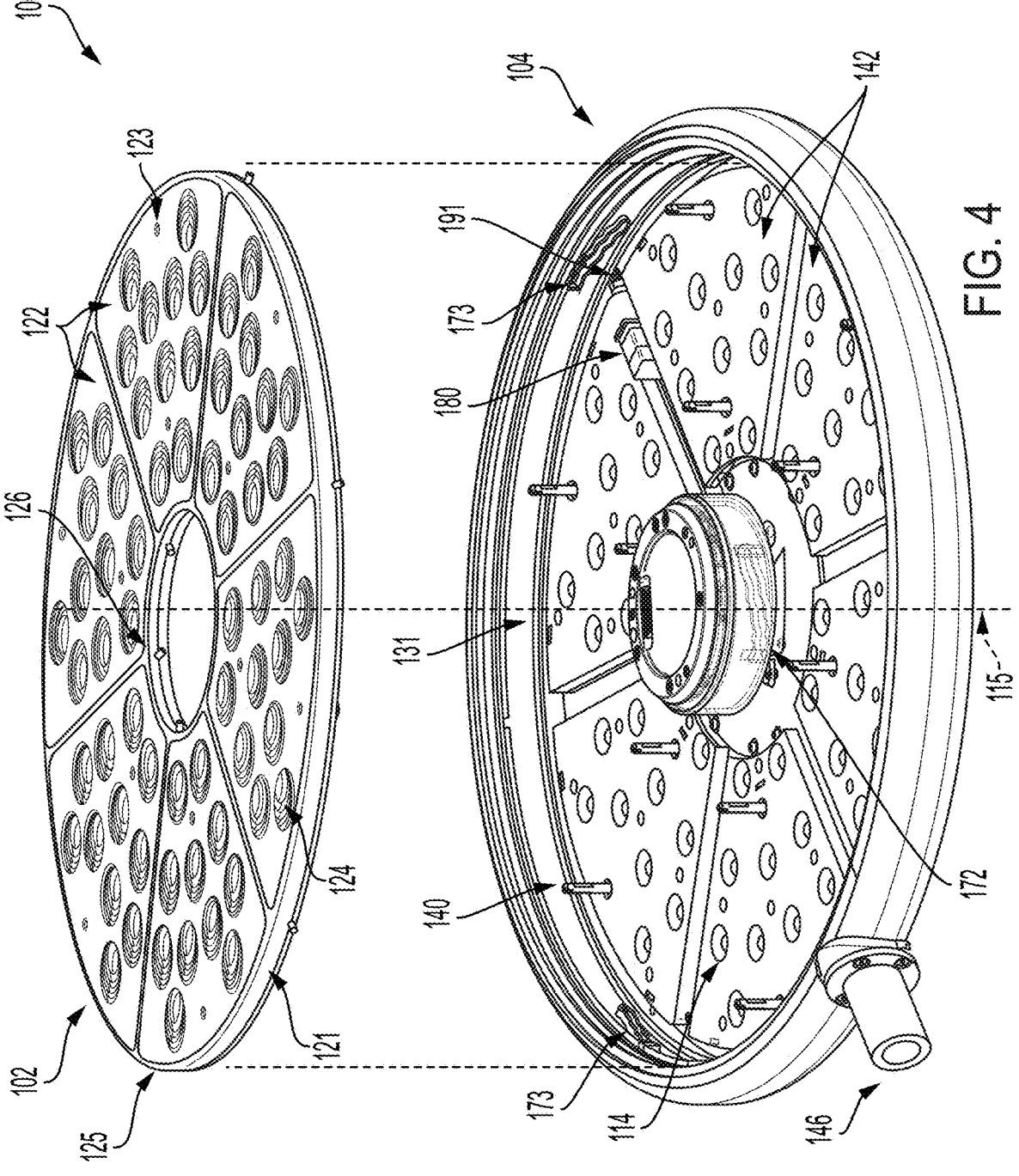
FIG. 4 shows an exploded view of exemplary focus panel and housing for a surgical light, according to one or more examples of the disclosure.

FIG. 4 shows an exploded view of exemplary focus panel 102 and housing 104 for a surgical light, according to one or more examples of the disclosure. As shown, the focus panel 102 includes a number of lens panels 122 arranged within a frame 121, with each lens panel 122 having a number of lenses 124. The lenses 124 of the focus panel 102 can collimate and/or redirect light that passes through the lenses 124. The lens panels 122 of the focus panel 102 can be mounted within the frame 121 such that each individual lens panel 122 can shift within the frame 121 laterally relative to the axis 115 such that each respective lens panel 122 can independently align in the lateral direction with the light emitters 106 and/or optical elements 114 via engagement of the respective lens panel 122 with its corresponding alignment pins 140. For example, with reference to FIG. 3, each lens panel 122 may include one or more retention features 127 (e.g., a resilient tab) that interfaces with a rim 129 of the frame 121 with a degree of lateral clearance to enable the lens panel 122 to shift laterally while retaining the lens panel 122 on the frame 121.

The housing 104 can be configured as discussed above and can be incorporated into a surgical light as discussed above. For instance, the housing 104 can be connected (as shown in FIG. 1) to an overhead boom in an operating room via the mounting interface 146 such that the surgical light 100 provides overhead light that illuminates a target area (e.g., of a patient on the table 15 of FIG. 1) in the operating room. As shown, the alignment pins 140 are arranged around the housing 104 and protrude orthogonally from the housing 104.

The alignment pins 140 arranged around the housing 104 are engaged with the housing panels 142 that contain light emitters (not shown). Each light emitter may be located behind one of the optical elements 114. The housing panels 142 can be mounted to the housing 104 such that the alignment pins 140 ensure each housing panel 142 is properly aligned within the housing 104. Each lens panel 122 can include one or more interface elements 123 that engage with alignment pins 140 mounted to the housing 104, as discussed above. The lens panels 122 of the focus panel 102 can correspond and align with each of the housing panels 142.

When the focus panel 102 is mounted on the housing 104, the engagement between each alignment pin 140 and a corresponding interface element 123 of the focus panel 102 can ensure both that the focus panel 102 remains aligned with and parallel to the optical components (e.g., light emitters 106 and optical elements 114 shown in FIG. 3) of the surgical light as the focus panel 102 is axially translated toward and away from the light emitters. Accordingly, the alignment pins 140 arranged around the housing 104, with each alignment pin 140 engaged with a housing panel 142 and a lens panel 122, can ensure that the optical elements of the surgical light (e.g., the light emitters, the optical elements 114, and the lenses 124 of the focus panel 102) remain aligned as the focus panel 102 axially translates toward or away from the light emitters.

The alignment pins 140 can also ensure that the focus panel 102 remains parallel to the housing panels 142 containing the light emitters. For instance, if the focus panel 102 moves away from the light emitters (upward as viewed in FIG. 4) the engagement between the focus panel 102 and the alignment pins 140 around the entirety of the housing 104 can ensure that the focus panel 102 uniformly travels up the alignment pins 140 without any tilting. Accordingly, by arranging the alignment pins 140 around the housing 104, the alignment pins 140 can ensure that the focus panel 102 remains parallel to the housing 104, ensuring the light redirected by the focus panel 102 is not distorted and provides a uniform wash of light over the target area being illuminated.

As shown in FIG. 4, the focus panel 102 can include a number of tabs. The focus panel 102 can include outer tabs 125 located on the outer perimeter of the focus panel 102. Additionally and/or alternatively, the focus panel 102 can include inner tabs 126 located on the inner perimeter of the focus panel 102. As discussed further below, one or more of the outer tabs 125 and/or the inner tabs 126 can engage a track that controls the axial translation of the focus panel 102. Each track can be movably mounted to a housing 104 and moved by an actuator (not shown in figure) such that as the track moves, the tab(s) of the focus panel 102 travel along the track, thereby axially translating the focus panel 102 toward or away from the light emitters to adjust the spot size of light provided by the surgical light.

Exemplary tracks are shown in FIG. 4, in which the housing 104 includes a number of peripherally-located peripheral tracks 173 provided in an annular outer ring 131. One or more of the outer tabs 125 of the focus panel 102 can be engaged with these peripheral tracks 173, such that if the peripheral tracks 173 move (e.g., via rotation of the outer ring 131), the outer tabs 125 of the focus panel 102 travel along the peripheral tracks 173, thereby axially translating the focus panel 102 toward or away from the light emitters. If the peripheral tracks 173 are moving counterclockwise with respect to the view of FIG. 4, for instance, the outer tabs 125 can travel along the peripheral tracks 173 to translate the focus panel 102 toward the light emitters. Alternatively, if the peripheral tracks 173 are moving clockwise, the outer tabs 125 can travel along the peripheral tracks 173 to translate the focus panel 102 away from the light emitters. As the outer tabs 125 of the focus panel 102 travel along the peripheral tracks 173 causing the focus panel 102 to translate, the alignment pins 140 can prevent the focus panel 102 from rotating. Thus, the engagement between the outer tabs 125 of the focus panel 102 and the peripheral tracks 173 can control the axial translation of the focus panel 102 while preventing rotation of the focus panel 102. Additionally, by including multiple peripheral tracks 173 to engage with the peripheral perimeter of the focus panel 102, the engagement between the outer tabs 125 of the focus panel 102 and the peripheral tracks 173 can ensure the focus panel 102 uniformly translates toward or away from the light emitters, thereby ensuring the focus panel 102 remains parallel to the light emitters.

Optionally, the peripheral tracks 173 may remain fixed, and the outer tabs 125 of the focus panel 102 can be driven along the peripheral tracks 173 via one or more actuators. In this example, the focus panel 102 may not be engaged with any alignment pins 140 (e.g. the surgical light 20 depicted in FIG. 2), and the focus panel 102 can be configured to rotate as the focus panel 102 moves toward or away from the light emitters of the surgical light. As the focus panel 102 rotates, the lenses 124 of the focus panel 102 may move from a first position, where each lens 124 is aligned with a first light emitter, to a second position, where each lens 124 of the focus panel 102 is aligned with a second light emitter. For instance, the focus panel 102 may initially be positioned such that the lenses 124 of the focus panel 102 are aligned with the optical elements 114 of a first housing panel 142, but after rotating while translating toward or away from the light emitters, the lenses 124 of the focus panel 102 may be aligned with the optical elements 114 of a second housing panel 142 that is adjacent the first housing panel 142. The outer tabs 125 of the focus panel 102 can be driven along the peripheral tracks 173 based on predefined intervals of rotation with each stopping point configured such that the lenses 124 of the focus panel 102 will be aligned with the optical components (e.g., the light emitters and optical elements 114) of the surgical light.

In addition or alternatively, one or more centrally-located central tracks 172 can similarly control the axial translation of the focus panel 102. One or more of the inner tabs 126 of the focus panel 102 can be inserted into a corresponding central track 172, and operate in the same manner—i.e., control the axial position of the focus panel 102 by the inner tabs 126 of the focus panel 102 traveling along the central tracks 172 and axially translating the focus panel 102 toward or away from the light emitters. Similarly, by including multiple central tracks 172 to engage with the central perimeter of the focus panel 102, the engagement between the inner tabs 126 of the focus panel 102 and the central tracks 172 can ensure the focus panel 102 uniformly travels toward or away from the light emitters, thereby ensuring the focus panel 102 remains parallel to the light emitters.

An actuator can control the movement of the tracks that engage the tabs of the focus panel 102. For example, one or more actuators 180 can engage the outer ring 131 (e.g., such as via a pinion of the actuator 180 driving a rack (not shown) of the outer ring 131). In FIG. 4, a single actuator 180 is located proximate to one of the peripheral tracks 173. It should be noted, however, that a surgical light according to the disclosure can include one or a plurality of actuators located peripherally relative to the focus panel 102, located centrally relative to the focus panel 102 (i.e., proximate to one of the central tracks 172), or both. The actuator 180 can be any suitable actuator that can be configured to control the movement of the tracks. For instance, the actuator 180 can be a stepper motor or a servo motor.

Figure 5:
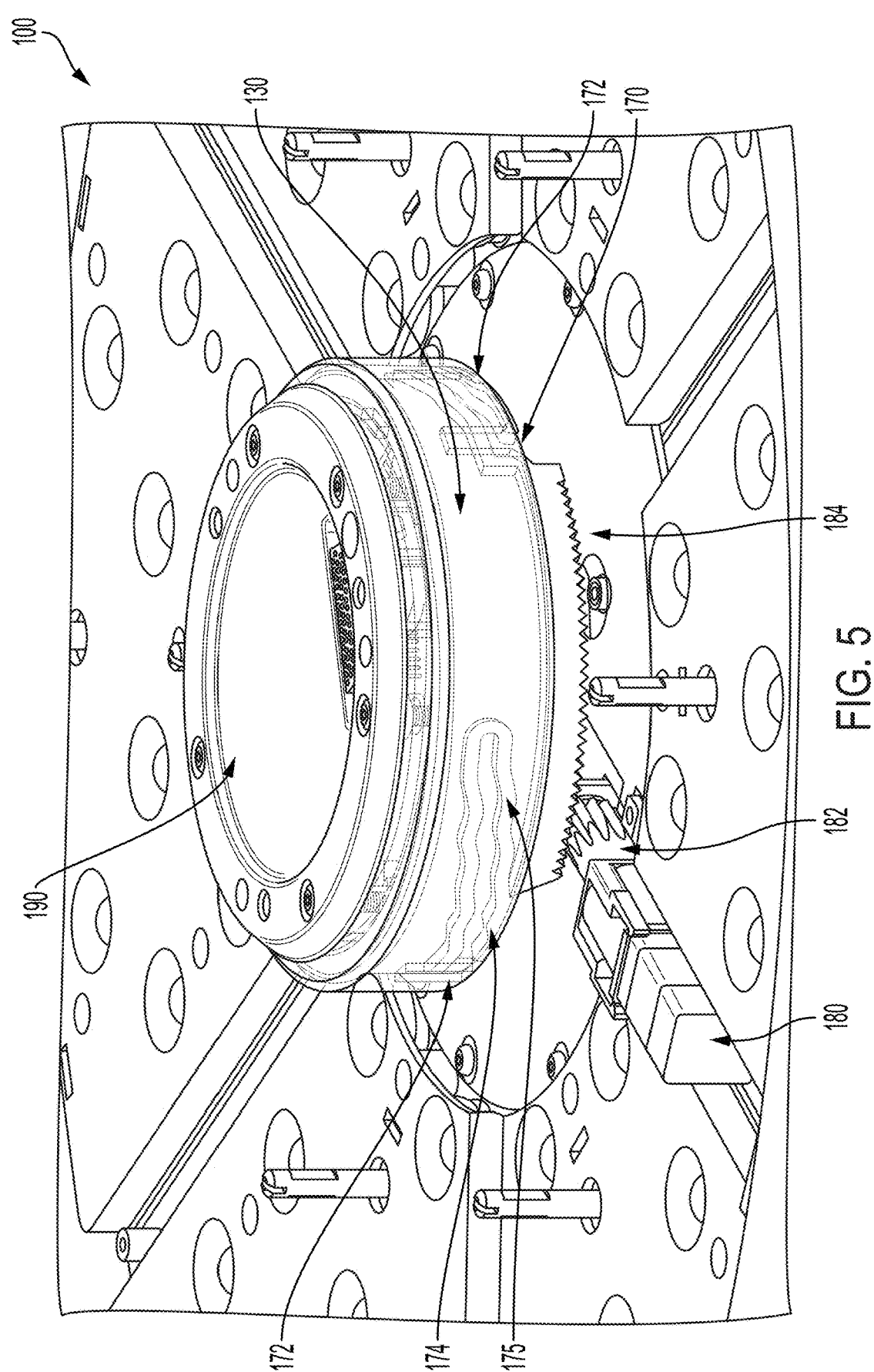
FIG. 5 show a detail view of an exemplary surgical light with focus mechanism comprising a centrally located track and actuator, according to one or more examples of the disclosure.

FIG. 5 shows a detail view of an exemplary surgical light 100 with a centrally located track and actuator. The surgical light 100 includes a central ring 130 around a hub 190, and the central ring 130 includes a central track 172 and a hub rack 184. The central ring 130 can be rotatably mounted to a housing of the surgical light 100. For instance, the hub rack 184 of the central ring 130 can be engaged with a pinion 182 of an actuator 180. The engagement between the hub rack 184 and the pinion 182 can cause the hub rack 184 to move as the pinion 182 rotates. Thus, the actuator 180 can cause the central ring 130 (and the central track 172) to rotate via the engagement between the hub rack 184 and the pinion 182. As the hub rack 184 moves in a counterclockwise direction, for example, the central track 172 can also move counterclockwise. Alternatively, as the hub rack 184 moves clockwise, the central track 172 can also move clockwise. Thus, the central track 172 can be part of a central ring 130 that is rotatably mounted to a housing of the surgical light 100.

Optionally, the central tracks 172 may remain fixed, and the tabs of the focus panel can be driven along the central tracks 172 via one or more actuators. In this example, the focus panel may not be engaged with any alignment pins, and the focus panel can be configured to rotate as the focus panel moves toward or away from the light emitters of the surgical light, as discussed above. As the focus panel rotates, the lenses of the focus panel may move from a first position, where each lens is aligned with a first light emitter, to a second position, where each lens of the focus panel is aligned with a second light emitter. The tabs of the focus panel can be driven along the central tracks 172 based on predefined intervals of rotation with each stopping point configured such that the lenses of the focus panel will be aligned with the optical components (e.g., the light emitters and optical elements) of the surgical light.

As the central track 172 moves, the central track 172 can be used to translate the focus panel toward or away from the light emitters of the surgical light 100. As shown in FIG. 5, the central track 172 includes an opening 170, which can receive a tab of the focus panel, such as the inner tabs 126 (shown in FIG. 4) discussed above. Once inserted, the tab of the focus panel can rest on a flat portion of the central track 172. If the central track 172 is moved, such as by the engagement between the pinion 182 and the hub rack 184, the movement of the central track 172 can cause the tab to travel along the central track 172, thereby axially translating the focus panel toward or away from the light emitters depending on the direction the central track 172 is moving. For example, if the hub rack 184 and central track 172 are moving counterclockwise, the tab can follow the central track 172 toward the light emitters. Conversely, if the hub rack 184 and the central track 172 are moving clockwise, the tab can follow the central track 172 away from the light emitters. Thus, the engagement between the tab of the focus panel and the central track 172 can cause the focus panel to translate axially toward or away from the light emitters, based on the movement of the central track 172.

As shown in FIG. 5, the central track 172 includes a number of ramped portions 175 and a number of flat portions 174. The ramped portions 175 of the central track 172 can drive the tab of the focus panel towards or away from the light emitters, and the flat portions 174 of the central track 172 can retain the tab of the focus panel in a given axial position relative to the light emitters. Thus, the central track 172 can both change the axial position of the focus panel and retain the axial position at a number of different distances relative to the light emitters of the surgical light 100 via the different portions of the central track 172. Rather than being stepped as shown in FIG. 5, the centrally-located central track 172 can include a straight track that does not have any flat portions 174, as will be discussed below. As shown in FIG. 5, the central ring 130 includes a plurality of central tracks 172 arranged in a circular configuration around the hub 190. The surgical light 100 also includes a single actuator 180 configured to move the central ring 130 as discussed above. Thus, the surgical light 100 can include a single actuator 180 configured to move a plurality of central tracks 172. Alternatively, the surgical light 100 can include a plurality of actuators 180. For instance, the surgical light 100 could include a plurality of actuators arranged around the hub 190, with each actuator including a pinion that engages with a corresponding hub rack 184 of the central ring 130. When the surgical light 100 includes a plurality of actuators, the actuators can be synchronized such that they move the central tracks 172 in unison, maintaining the focus panel in parallel with respect to the housing of the surgical light as the focus panel is raised or lowered. Optionally, the surgical light can include three central tracks 172 separated by 120 degrees relative to one another around the hub 190.

The flat portions 174 of the central track 172 can help maintain the parallelism of the focus panel relative to the light emitters of the surgical light. When the surgical light incorporates a plurality of actuators, the flat portions 174 can also help account for tolerances in the synchronization of those actuators. The flat portions 174 can also help account for dimensional tolerances of the various components of the surgical light.

Although FIG. 5 shows that the central ring 130 comprising the central tracks 172 is centrally located, the surgical light can additionally or alternatively include a peripherally located ring that comprises tracks that engage the tabs of the focus panel, such as described above with respect to outer ring 131 and peripheral tracks 173 of FIG. 4.

Figure 6:
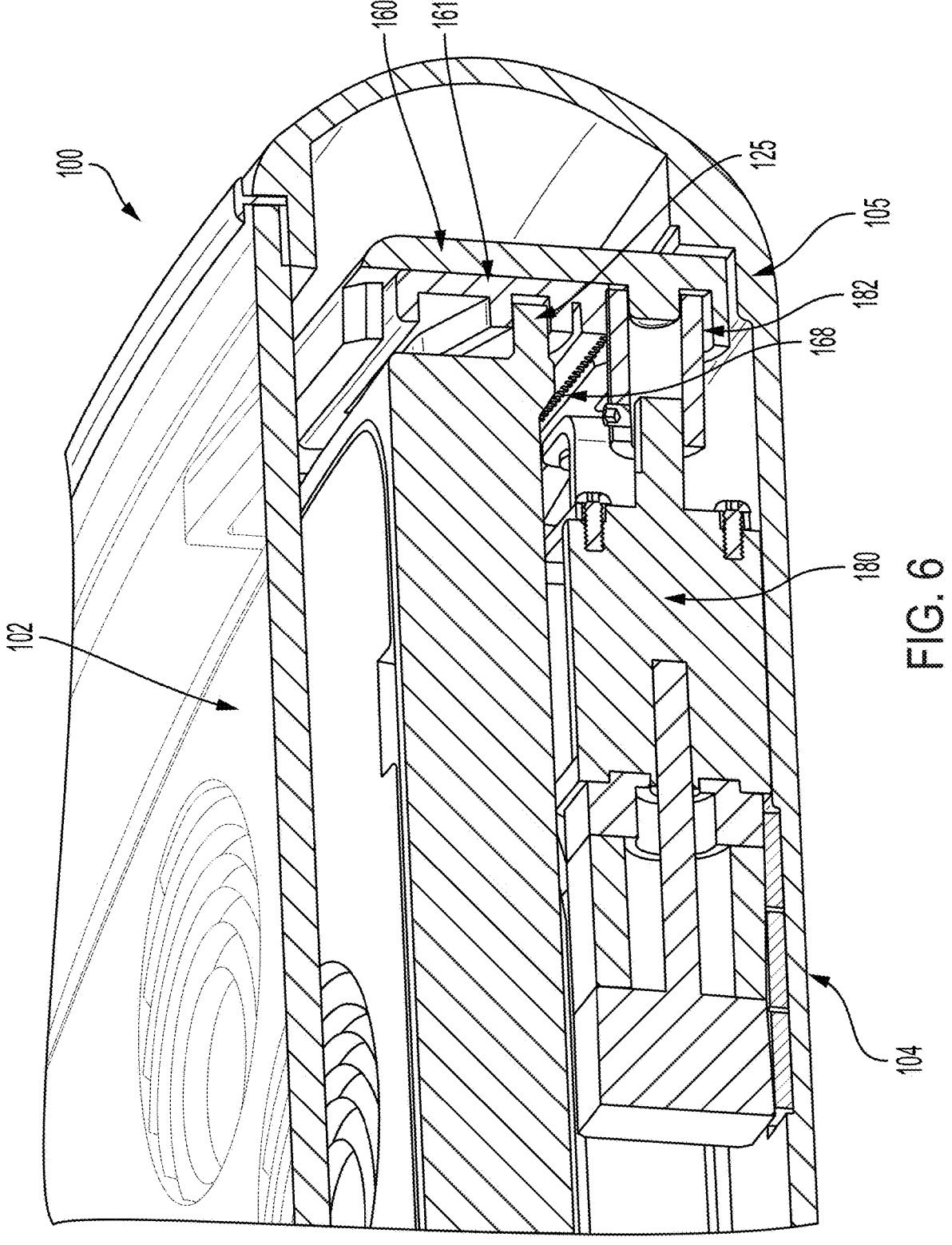
FIG. 6 shows a detail view of the perimeter of an exemplary surgical light with a focus mechanism with a slider mechanism and dedicated actuator, according to one or more examples of the disclosure.

Another configuration for translating a focus panel of a surgical light can include slider mechanisms located at the periphery or center of a housing of the surgical light that engage with the focus panel. FIG. 6 shows a detail view of the periphery of an exemplary surgical light 100, such as the surgical lights discussed above. As shown, an outer tab 125 of a focus panel 102 is engaged with a slider mechanism 160 that is engaged with an actuator 180. The slider mechanism 160 can be mounted to an interior wall 105 of the housing 104 of the surgical light such that the slider mechanism 160 is fixed. The outer tab 125 of the focus panel 102 can be engaged with a track of a sliding panel 161 of the slider mechanism 160 with the sliding panel 161 configured to move relative to the housing 104 of the surgical light.

As will be described below, the slider mechanism 160 can include a rack 168 that is engaged with a pinion 182 of the actuator 180, with the rack 168 configured to move the sliding panel 161 of the slider mechanism 160 to axially translate the focus panel 102 toward or away from the light emitters of the surgical light.

Though FIG. 6 depicts only one actuator 180 and slider mechanism 160, this configuration can be repeated a number of times around the focus panel 102 to ensure the focus panel 102 maintains a stable position and remains parallel with respect to the light emitters and the housing 104. For example, the surgical light 100 can include three separate slider mechanisms 160 positioned 120 degrees relative to one another around the periphery of the focus panel 102 each engaged with an outer tab 125 of the focus panel 102. The three slider mechanisms 160 can define a plane for maintaining parallelism of the focus panel 102 as the focus panel 102 is axially translated toward or away from the light emitters of the surgical light 100. When the surgical light 100 includes a plurality of actuators, the actuators can be synchronized such that they move the sliding panels 161 of the slider mechanisms 160 (and the tracks engaged with the tabs of the focus panel) in unison, maintaining the focus panel 102 in parallel with respect to the housing 104 as the focus panel 102 is axially translated toward or away from the light emitters of the surgical light 100. Optionally, the surgical light can include a plurality of slider mechanisms 160 on the periphery of the focus panel 102, but not incorporate a dedicated actuator for each slider mechanism 160, as will be discussed below.

Figures 7, 8:
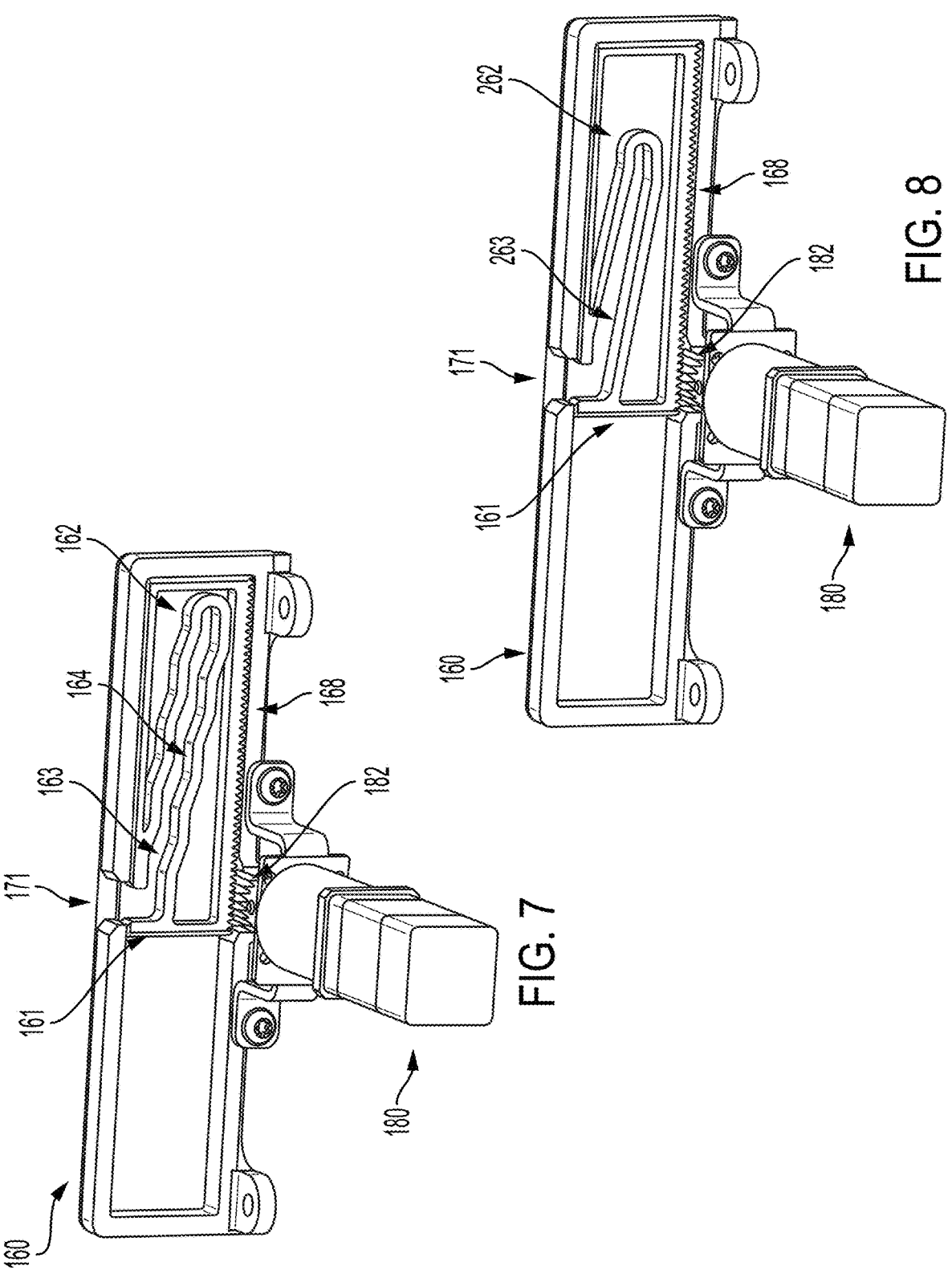
FIG. 7 shows an exemplary slider mechanism with a stepped track for a surgical light with a focus mechanism, according to one or more examples of the disclosure.
FIG. 8 shows an exemplary slider mechanism with a straight track for a surgical light with a focus mechanism, according to one or more examples of the disclosure.

An example of a slider mechanism 160 is shown in FIG. 7. The slider mechanism 160 can be fixedly attached to the housing of a surgical light along the periphery of a focus panel engaged with the housing (e.g., as shown in FIG. 6), such that an outer tab of the focus panel (e.g., outer tab 125 shown in FIG. 6) is engaged with the slider mechanism 160.

The sliding panel 161 can include a rack 168 that translates rotational movement of a pinion 182 into movement of the sliding panel 161 (i.e., leftward or rightward with respect to the view shown in FIG. 7). For instance, if the pinion 182 rotates in a counterclockwise direction, the engagement between the rack 168 and the pinion 182 can cause the sliding panel 161 to move to the left (as shown in FIG. 7). Alternatively, if the pinion 182 rotates in a clockwise direction, the engagement between the rack 168 and the pinion 182 can cause the sliding panel 161 to move to the right.

As shown in FIG. 7, the sliding panel 161 can include a stepped track 162 with an opening 171. The opening 171 can allow insertion of a tab of a focus panel, such as the inner tab or the outer tab of the focus panel discussed above. Once inserted, the tab of the focus panel can rest on a flat portion 164 of the stepped track 162. If the sliding panel 161 is moved, such as by the engagement between the pinion 182 and the rack 168, the stepped track 162 can cause the tab to follow the stepped track 162 either toward or away from the light emitters of the surgical light, depending on the direction the rack 168 is moving. For example, if the rack 168 is moving to the left, the tab can follow the stepped track 162 toward the light emitters of the surgical light. Alternatively, if the rack 168 is moving to the right, the tab can follow the stepped track 162 away from the light emitters of the surgical light. Thus, the engagement between the tab of the focus panel and the stepped track 162 of the sliding panel 161 can cause the focus panel to translate axially toward or away from the light emitters, based on movement of the stepped track 162.

The stepped track 162 can include a number of ramped portions 163 and a number of flat portions 164. As discussed above, the ramped portions 163 can be used to drive the tab of the focus panel assembly toward or away from the light emitters of the surgical light based on the direction the sliding panel 161 is translating. Conversely, the flat portions 164 can be used to retain the tab of the focus panel in a given axial position relative to light emitters of the surgical light. Thus, the stepped track 162 can be used to change the axial position of the focus panel relative to the light emitters and to retain the axial position at a number of different distances relative to the light emitters of the surgical light via the different flat portions 164 of the stepped track 162. The flat portions 164 can correspond to preset spot sizes of light provided by the surgical light.

Optionally, the slider mechanism 160 can also include a retaining panel (not shown) that is provided on a front face of the sliding panel 161 such that the sliding panel is sandwiched between front and back retaining panels but permitted to slide within the space between them. The front retaining panel can include a centrally located notch that enables the tab of the focus panel to be inserted into the opening 171 of the sliding panel 161. Such a notch can extend substantially along the height of the retaining panel such that the tab is permitted to follow the stepped track 162 as discussed above, but can be relatively narrow such that the tab travels only toward or away from the light emitters of the surgical light. Thus, the notch of the retaining panel can ensure that the focus panel does not rotate relative to the housing of the surgical light. However, the focus panel can be prevented from rotating without requiring a retaining panel, such as by the alignment pins discussed above.

FIG. 8 shows an exemplary slider mechanism 160 that can be used, for example, for slider mechanism 160 of FIG. 6. As compared to the slider mechanism 160 of FIG. 7, the sliding panel 161 of the slider mechanism 160 in FIG. 8 has a straight track 262, rather than the stepped track 163. Once the tab of the focus panel is inserted via the opening 171, the tab can rest on a ramped portion 263 of the straight track 262. If the sliding panel 161 is moved, such as by the engagement between the pinion 182 and the rack 168, the straight track 262 can cause the tab to follow the straight track 262 either toward or away from the light emitters of the surgical light, depending on the direction the rack 168 is moving. Thus, the engagement between the tab of the focus panel and the straight track 262 can cause the focus panel to translate axially toward or away from the light emitters, based on the movement of the straight track 262.

As shown, the straight track 262 includes a single ramped portion 263 that extends along the length of the straight track 262. The ramped portion 263 can be used to drive the tab of the focus panel assembly toward or away from the light emitters of the surgical light based on the direction the sliding panel 161 is translating. The tab can be stopped at a location between the ends of the ramped portion 263. For example, a tab of the focus panel inserted into the opening 171 can be driven partway along the straight track 262 as discussed above, but then retained in such position because the actuator has stopped rotating the pinion 182 but the pinion 182 remains engaged with the rack 168 thereby preventing any further movement of the sliding panel 161. The tab of the focus panel can additionally or alternatively be retained in a position between the ends of the ramped portion 263 via a brake, such as a brake integrated in the actuator 180. A tab can be stopped at any location between the ends of the ramped portion 263, which facilitates adjusting the spot size of light provided by the surgical light as necessary without requiring preset spot sizes. Thus, the straight track 262 can be used to change the axial position of the focus panel relative to the light emitters and to retain the axial position at a number of different distances relative to the light emitters of the surgical light.

As with the slider mechanism 160 of FIG. 7, the slider mechanism 160 of FIG. 8 can optionally include a retaining panel (not shown) that is provided on a front face of the sliding panel 161 such that the sliding panel is sandwiched between front and back retaining panels but permitted to slide within the space between them. The front retaining panel can include a centrally located notch that enables the tab of the focus panel to be inserted into the opening 171 of the sliding panel 261. Such a notch can extend substantially along the height of the retaining panel such that the tab is permitted to follow the straight track 262 as discussed above, but can be relatively narrow such that the tab travels only toward or away from the light emitters of the surgical light. Thus, the notch of the retaining panel can ensure that the focus panel does not rotate relative to the housing of the surgical light. The focus panel can be fixed and prevented from rotating without requiring a retaining panel, such as by the alignment pins discussed above.

A surgical light according to the disclosure herein can include a plurality of slider mechanisms each with their own dedicated actuator. For example, the surgical light can include three separate slider mechanisms separated by 120 degrees relative to one another along the periphery of the focus panel, each including a dedicated actuator. Alternatively, a surgical light according to this disclosure may include a plurality of slider mechanisms, but each slider mechanism may not have a dedicated actuator, as will be described below.

Figure 9:
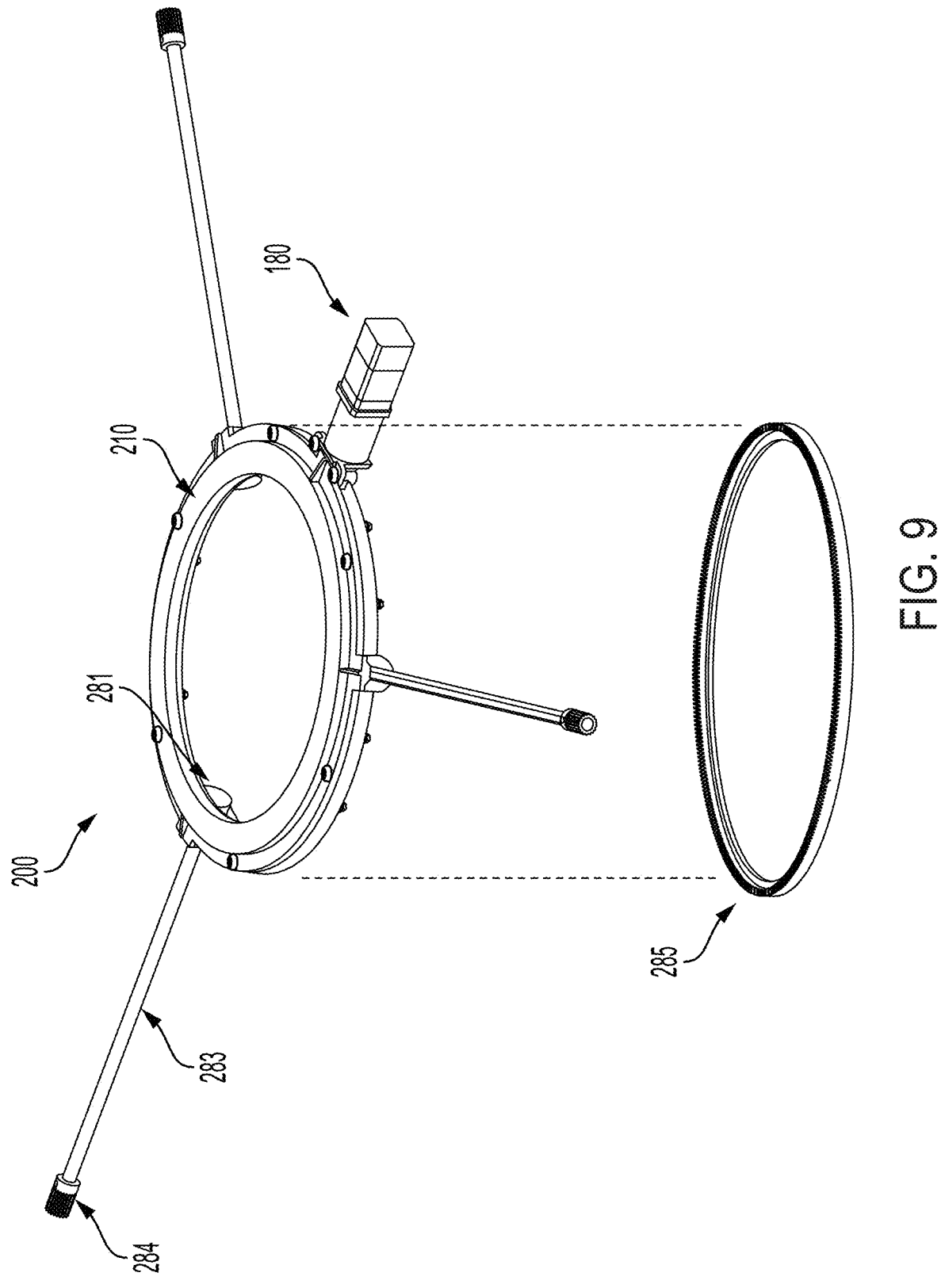
FIG. 9 shows an exemplary center actuator assembly for a surgical light, according to one or more examples of the disclosure.

FIG. 9 shows an exemplary center actuator assembly 200 that can incorporate a ring-shaped rack 285. As shown in FIG. 9, the center actuator assembly 200 includes a plurality of rods 283 that extend outwardly from the cover plate 210. The center actuator assembly 200 can include outer pinions 284 (one for each peripheral slider mechanism 160) and an inner pinion 281. The ring-shaped rack 285 can engage the inner pinions 281 of the rods 283, and can be moved (e.g., rotated) by the actuator 180 in order to rotate the rods 283. For example, the ring-shaped rack 285 can be located adjacent to the cover plate 210 and engaged with the inner pinions 281 of each rod 283. The actuator 180 includes a pinion (not shown in figure) that engages with a ring-shaped rack 285 beneath the cover plate 210, with the ring-shaped rack 285 also engaged with the inner pinion 281 of each rod 283. The inner pinion 281 and outer pinion 284 of the rod 283 can be fixed relative to the rod 283 such that they rotate in unison with one another. Thus, as the pinion of the actuator 180 rotates, the ring-shaped rack 285 can rotate, which in turn causes the rods 283 to rotate.

As shown in FIG. 9, the center actuator assembly 200 includes three rods 283. This should not be construed to be limiting, however, as the center actuator assembly 200 can include a corresponding number of rods 283 to engage with the number of slider mechanisms of the light. In any case, a surgical light according to the disclosure can be configured such that a ring-shaped rack drives a plurality of rods that in turn drive a plurality of tracks.

Figure 10:
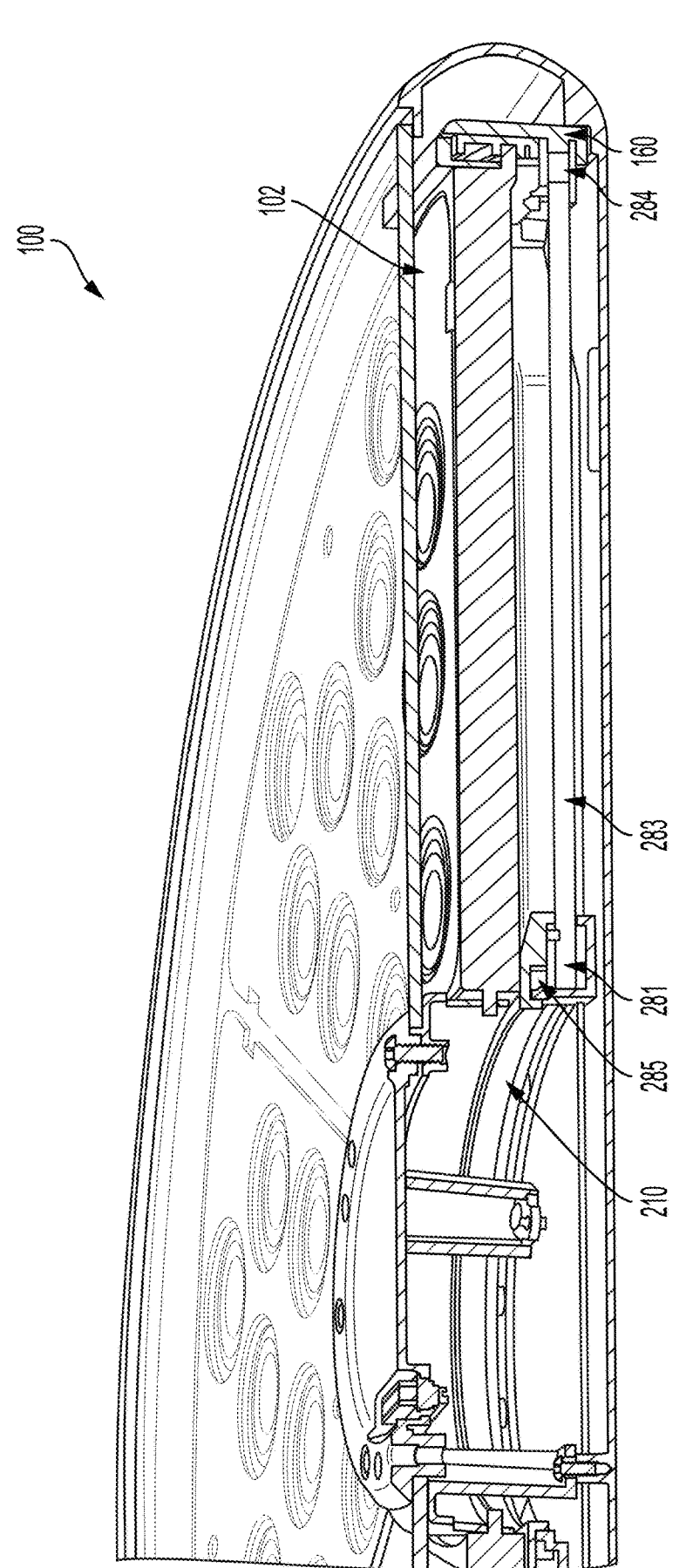
FIG. 10 shows a cutaway view of an exemplary surgical light with a center actuator assembly, according to one or more examples of the disclosure.

The rods 283 of the center actuator assembly 200 can be engaged with the slider mechanisms discussed above. An example of this is shown in FIG. 10, which depicts an exemplary surgical light 100 with a center actuator assembly, such as the center actuator assembly 200 of FIG. 9. As shown, the rod 283 of the center actuator assembly extends outwardly and drives outer pinion 284, which engages with the slider mechanism 160. The inner pinion 281 of the rod 283 can engage with a ring-shaped rack 285. The ring-shaped rack 285 can be driven via the actuator 180 and thereby drive rotation of the rod 283. The outer pinion 284 of the rod 283 can engage the slider mechanism 160. The outer pinion 284 can be engaged with a rack of the slider mechanism that translates the rotational movement of the outer pinion 284 into movement of a sliding panel on the slider mechanism 160, with the movement of the track configured to axially translate the focus panel 102 toward or away from the light emitters of the surgical light 100.

To facilitate controlling the spot size, the surgical light can include a controller for controlling the one or more actuators of the surgical light. As discussed above, the movement of the actuators can be capable of moving at least one track that is engaged with a tab of the focus panel assembly, such that as the actuators move, the focus panel is axially translated toward or away from the light emitters, thereby adjusting the spot size of light provided by the surgical light. Thus, the surgical light according to the disclosure can rely on one or more controllers to adjust the spot size of light provided by the surgical light.

Figure 11:
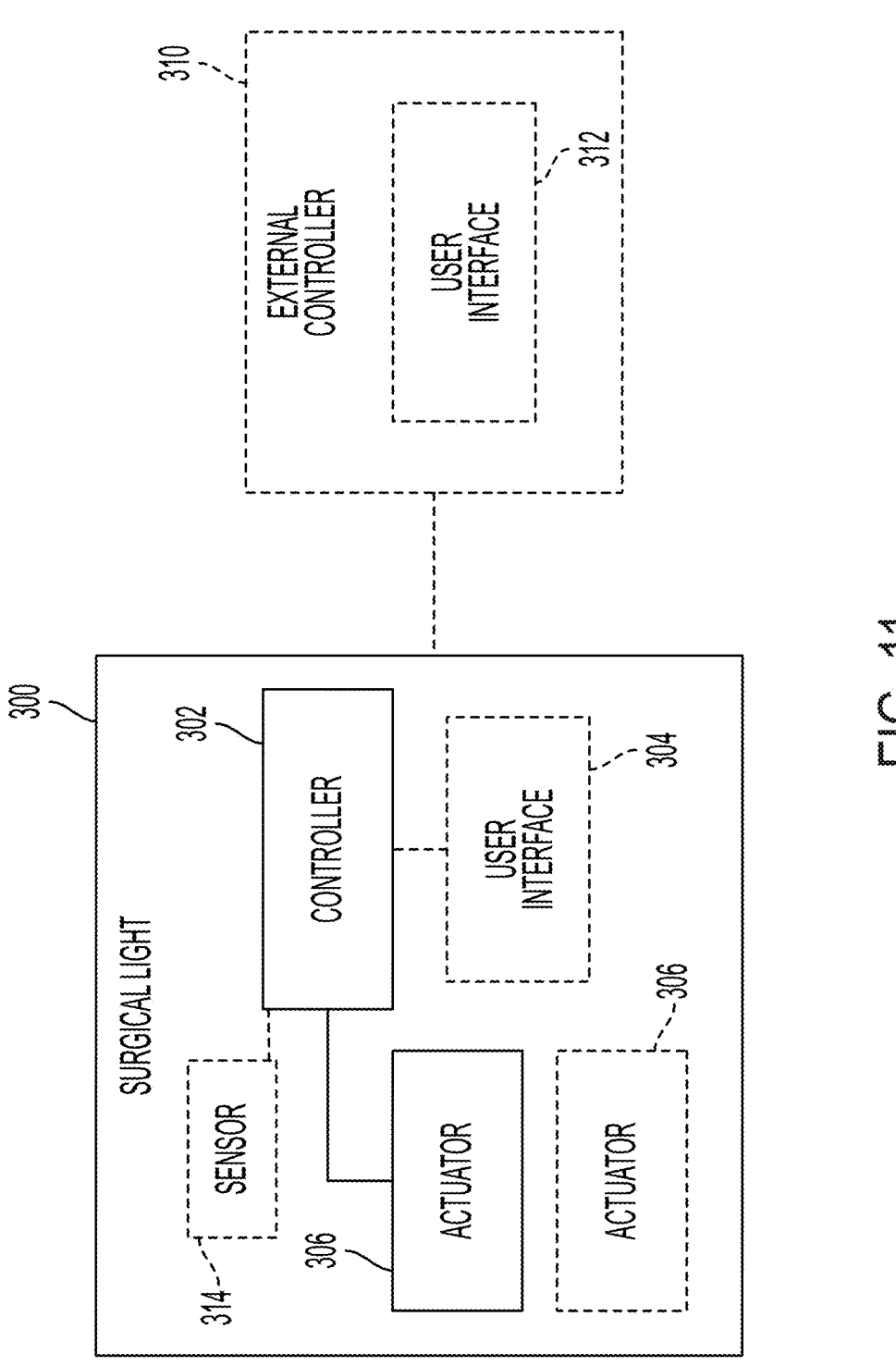
FIG. 11 shows a block diagram of a system for adjusting a spot size of light provided by a surgical light with a focus mechanism, according to one or more examples of the disclosure.

FIG. 11 shows a block diagram of a system for adjusting a spot size of light provided by a surgical light with a focus mechanism. As shown, the surgical light 300 includes a controller 302 and at least one actuator 306. The surgical light 300 can include one actuator 306, or a plurality of actuators 306, as discussed with reference to the surgical lights discussed above. The controller 302 can be configured to control one or more actuators 306, depending on how many actuators 306 are incorporated into the surgical light 300.

The controller 302 can be communicatively coupled to a user interface. The user interface can be located on the surgical light itself, as shown by the coupled user interface 304, or can be externally located remotely of the surgical light, as shown by the external controller 310. A coupled user interface 304 can be located, for example, on an exterior of the housing of the surgical light (e.g., user interface 14 in FIG. 1), on a handle coupled to the surgical light, etc. An external controller 310 may be located in the operating room in which the surgical light 300 is deployed (as shown in FIG. 1), or outside of the operating room and/or hospital altogether and may include a user interface 312 for enabling a user to adjust the spot size of the surgical light 300 (e.g., user interface 12 in FIG. 1). The external controller 310 can be or include any computing device, such as a smart phone, edge computing device, cloud computing device, and/or any other computing device suitable receiving commands from a user via a user interface 312. The external controller 310 could be a wall-mounted controller located in the operating room, in a neighboring operating room, conference room, auditorium, and/or any other location suitable for receiving commands from a user via a wall-mounted controller.

The external controller 310 can send a command (such as based on user input to the user interface 312 by a user) to the controller 302 of the surgical light 300. After receiving the command, the controller 302 of the surgical light 300 can cause the actuator(s) 306 to move one or more tracks of the surgical light 300, thereby axially translating a focus panel and adjusting the spot size of light provided by the surgical light 300, as discussed above. Similarly, the controller 302 can receive a command from a user via the user interface 304 and control the actuator(s) 306 to move one or more tracks of the surgical light 300, thereby axially translating a focus panel and adjusting the spot size of light provided by the surgical light 300. The surgical light may include one or more sensors 314 for providing feedback to the controller 302 associated with a position of the focus panel, which the controller 302 may use to control the actuator(s) 306 to move the focus panel to one or more predetermined positions.

Figure 12:
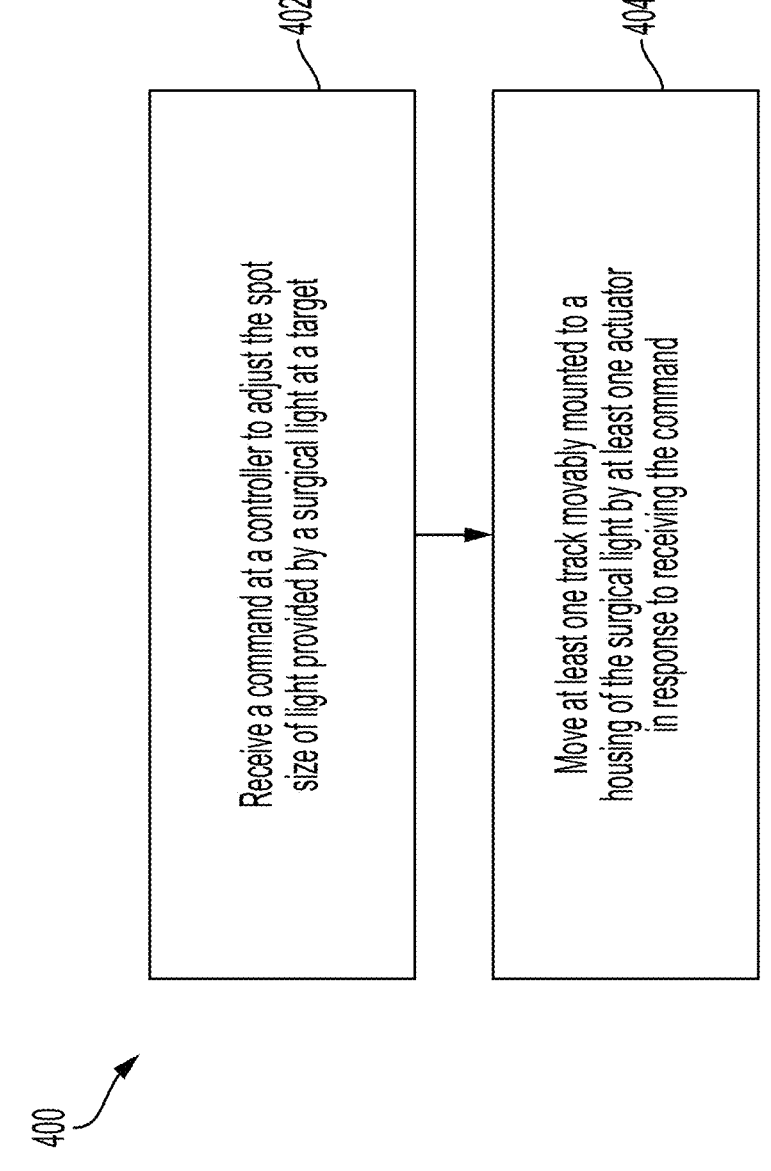
FIG. 12 shows an exemplary process for adjusting a spot size of light provided by a surgical light with a focus mechanism, according to one or more examples of the disclosure.

FIG. 12 shows an exemplary process 400 for adjusting a spot size of light provided by a surgical light with a focus mechanism, such as by the surgical lights discussed above. The process 400 can begin at step 402, with receiving a command at a controller of the surgical light to adjust the spot size of light provided by the surgical light at a target. The command received at step 402 can be received from a user via a user interface, such as any one of the user interfaces discussed above. The command received at step 402 can be executed by a user via a user interface that is coupled to the surgical light, or via a user interface that is external to but communicatively coupled to the surgical light. The user interface can include, for example, icons corresponding to pre-set spot size values, such that the user can select one of the icons corresponding to a pre-set spot size to command the controller to adjust the spot size according to that spot size. For instance, the user interface can include selectable icons corresponding to a small spot size, a medium spot size, and a large spot size, with the controller configured to adjust the spot size of the light provided by the surgical light according to those pre-set spot size if the user selects a given icon. Optionally, the command at step 402 may be received from an external system based on the external system configuring the surgical light according to a predetermined spot size configuration associated with, for example, a type of surgical procedure, a room setup, and/or a surgeon profile. After receiving a command at step 402, the process 400 can move to step 404 and move at least one track movably mounted to a housing of the surgical light by at least one actuator. Moving the track(s) at step 404 can occur in response to the command received at step 402. Moving the track(s) at step 404 can involve any of the methods discussed above. For instance, moving the track(s) at step 404 can involve controlling one or more actuators to move a pinion that is engaged with a rack or ring-shaped rack that can then cause a track that is engaged with a tab of a focus panel to travel along the track towards or away from the light emitters of the surgical light, thereby causing the focus panel to axially translate toward or away from the light emitters of the surgical light.

The command received at step 402 can correspond to one or more predefined focus settings and the surgical light can be configured to move one or more tracks a predefined amount that is associated with the predefined focus setting. For instance, the surgical light can have a predefined focus setting that involves moving the focus panel of the surgical light a specified distance toward or away from the light emitters, such as moving the focus panel 2 mm away from the light emitters. The predefined focus setting can also be based on certain distances, with a predefined focus setting corresponding to the focus panel being a certain distance away from the light emitters. For instance, rather than moving the focus panel 2 mm away from the light emitters, the surgical light may move the focus panel whatever distance is necessary to ensure the focus panel is located 2 mm from the light emitters, which could be determined, for example, by one or more sensors (e.g., sensor(s) 314 of FIG. 11). Thus, in response to receiving a command corresponding to a predefined focus setting at step 402, the moving the track(s) at step 404 can involve moving the track(s) whatever distance is necessary such that the focus panel is separated from the light emitters by a specified distance.

Moving the track(s) at step 404 can include moving the track(s) based on feedback from one or more sensors associated with one or more positions of the track(s). For example, the controller (e.g., controller 302 of FIG. 11) can activate the actuator(s) to move the track(s) until the output from one or more sensors indicates that the track(s) have reached a predetermined position that corresponds to a predetermined position of the focus panel. In response to receiving the output from the one or more sensors, the controller can control the actuator to stop movement of the track(s) so that the focus panel remains in the predetermined position relative to the light emitters.

Figure 13A:
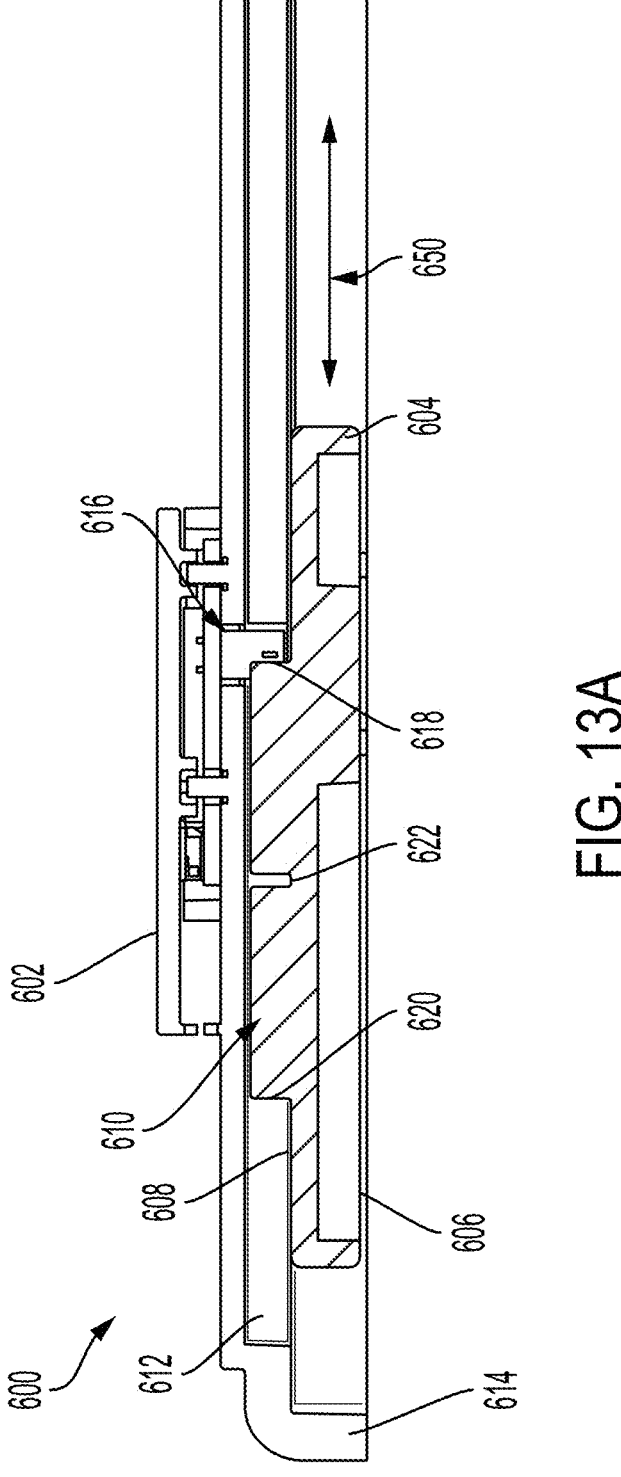
FIG. 13A illustrates an example of a slider mechanism that includes a sensor module for providing feedback associated with the position of a track of the slider mechanism.

FIG. 13A illustrates an example of a slider mechanism 600 that includes a sensor module 602 for providing feedback to a controller (e.g., controller 302 of FIG. 11) associated with the position of a track of the slider mechanism. FIG. 13A is a cross-section of the slider mechanism 600 along a plane that bisects the slider mechanism 600. The movement direction 650 of the slider mechanism 600 is indicated to help clarify the orientation of the cross-section. Slider mechanism 600 can be configured similarly to slider mechanism 160 of FIGS. 6-8. Slider mechanism 600 includes a sliding panel 604 having a track 606, which can be similar to sliding panel 161 and track 162 of FIG. 7. Extending from the back side 608 of the sliding panel 604 is a rib 610. The rib 610 may ride in a slot 612 of a housing 614 of the slider mechanism 600. The sensor module 602 can include a sensor 616 that interfaces with the rib 610. The sensor 616 may be configured to provide an output that is associated with one or more positions of the rib 610 in the movement direction 650 of the sliding panel 604. For example, the sensor 616 may be configured to provide an output that varies when one or more features of the rib 610 are aligned with the sensor, thus providing an output that indicates a position of the sliding panel 604.

In the illustrated example, the sensor 616 is an optical sensor that provides one output when an optical pathway is blocked by the rib 610 and a different output when the optical pathway is not blocked by the rib 610. When the sliding panel 604 travels sufficiently to the left in FIG. 13A, a first end 618 of the rib 610 can escape the optical pathway of the sensor 616. The output from the sensor 616 will change in accordance with the rib 610 no longer blocking the light pathway of the sensor 616, thus providing feedback to a connected controller that the sliding panel 604 is at a position associated with the first end 618 of the rib 610 being just past the optical pathway of the sensor 616. Similarly, when the sliding panel 604 travels sufficiently to the right in FIG. 13A, a second end 620 of the rib 610 can escape the optical pathway of the sensor 616 resulting in the output from the sensor 616 corresponding to a position of the sliding panel 604 that is associated with the second end 620 of the rib 610 being just past the optical pathway of the sensor 616.

The rib 610 may include one or more gaps 622 between the first and second ends 618, 620 that provide more positions for sensing by the sensor 616. In the illustrated example, a single gap 622 is provided, thus enabling the sensor to detect an additional, intermediate position of the sliding panel 604. However, this is merely exemplary, and it will be understood by a person of skill in the art that any desired number of positions can be detected by including an appropriate number of gaps 622.

Figure 13B:
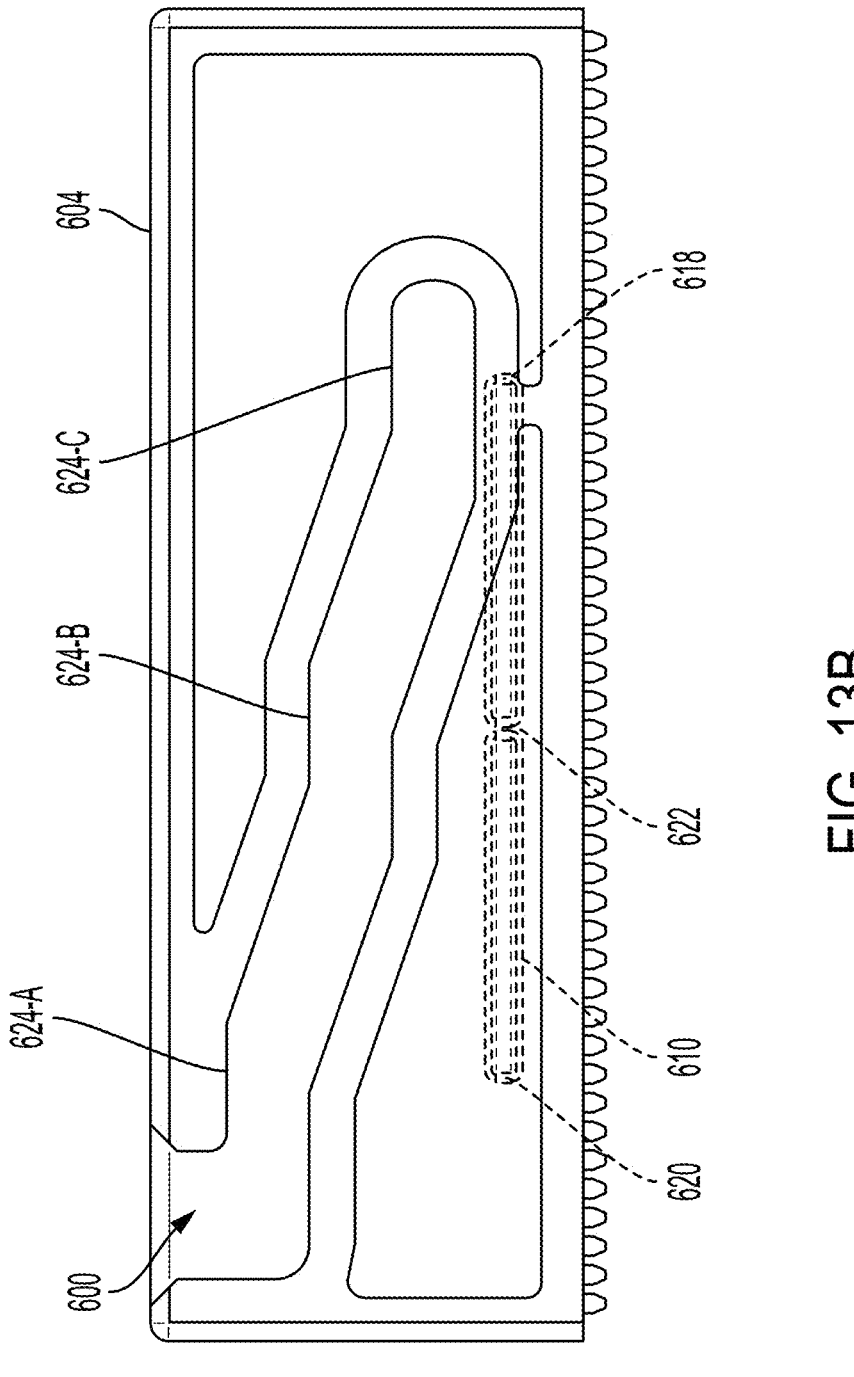
FIG. 13B is a side view of sliding panel of the slider mechanism of FIG. 13A.

FIG. 13B is a side view of sliding panel 604 illustrating alignment of the first and second ends 618, 620 and gap 622 of the rib 610 with corresponding portions of the track 606. This correspondence between the ends of gap(s) of rib 610 with the track 606 enables the output of the sensor 616 to correspond to predetermined positions of a focus panel since the focus panel rides along the track 606 (as discussed above with respect to the engagement between focus panel 102 and slider mechanism 160). Thus, in the illustrated example, the output from the sensor module 602 can be used by the controller to position a focus panel in three predetermined positions—position 624-A, position 624-B, and position 624-C.

Figure 13C:
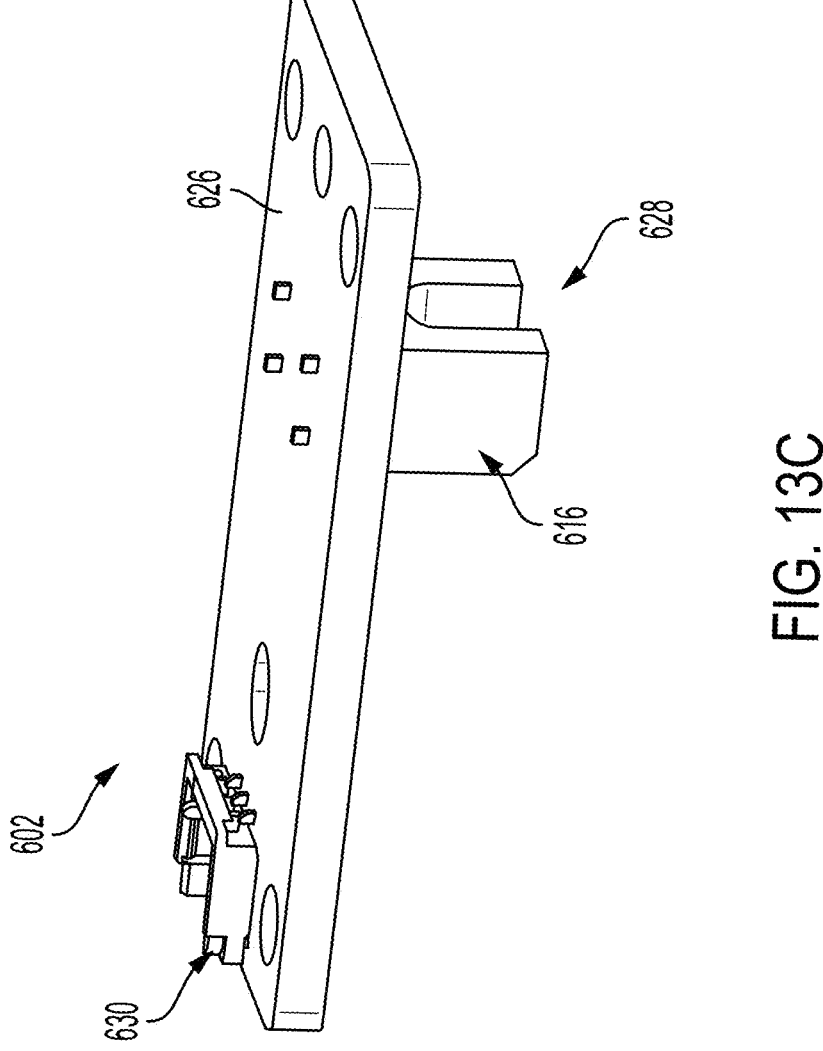
FIG. 13C illustrates an example of a sensor module for the slider mechanism of FIG. 13A.

FIG. 13C illustrates an example of sensor module 602. Sensor module 602 includes sensor 616 mounted to a printed circuit board 626. The sensor 616 includes a slot 628 within which rib 610 slides. A light beam is emitted by the sensor 616 that can span the slot 628 when not blocked by the rib

610. The output of the sensor 616 can vary based on whether the light beam is detected or not. The sensor module 602 can include a connector 630 for connecting a cable (not shown) that may extend to a controller (e.g., controller 302 of FIG. 11).

Although the above examples refer to an optical sensor, this is merely an example of the types of sensors that may be used to provide feedback associated with a position of the sliding panel 604. It should be understood that many different types of sensors may be used. For example, a Hall Effect sensor may be used to detect the alignment with a suitable metallic portion of the sliding panel 604. Additionally or alternatively, one or more limit switches may trigger when the sliding panel 604 is in predetermined positions. Other examples of suitable sensors include proximity sensors, time-of-flight sensors, resistive potentiometers, magnetic potentiometers, photomicro sensors, and/or encoders that count a number of turns of a motor.

Figure 14:
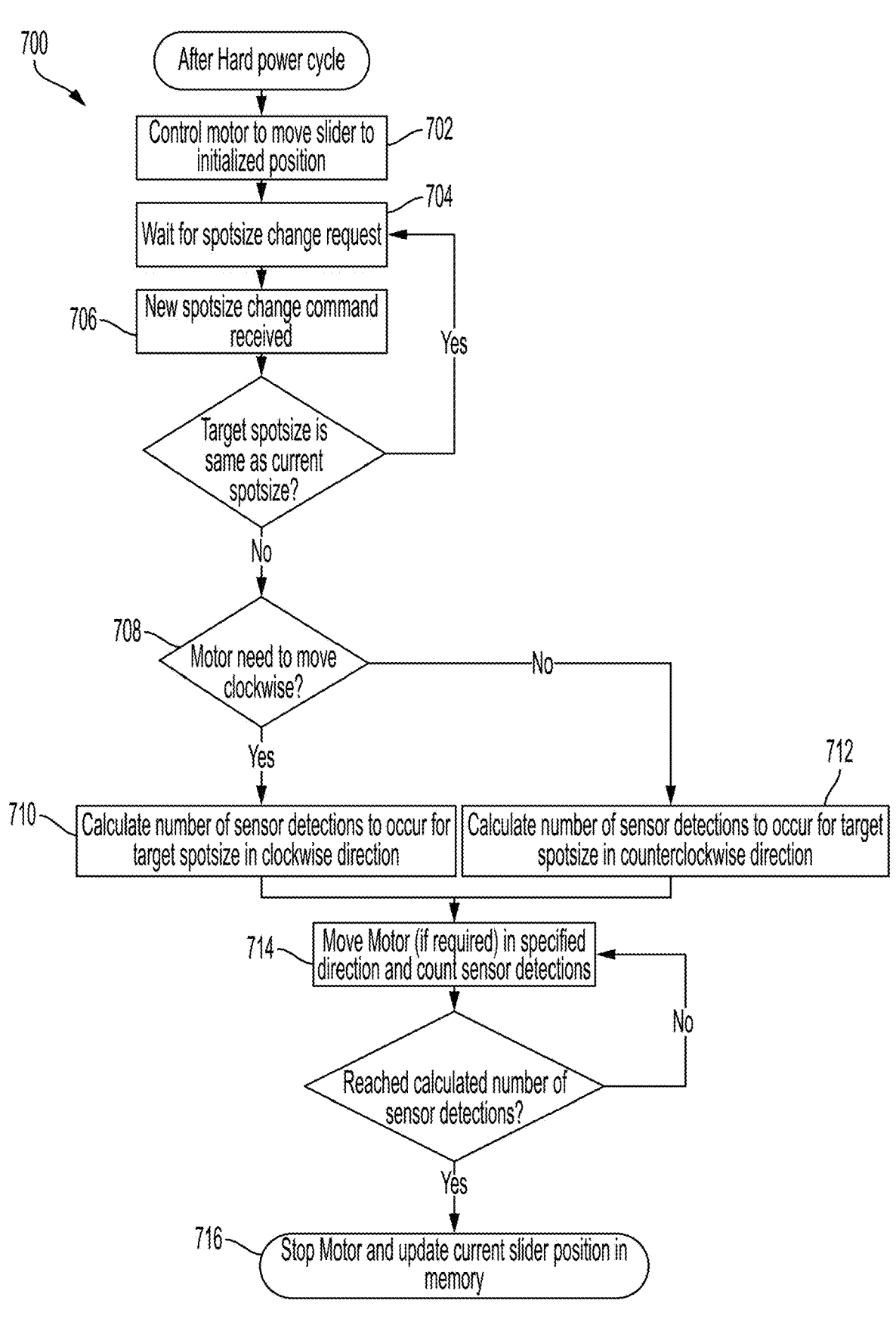
FIG. 14 is a flow diagram of an exemplary method for controlling the position of a sliding panel of a slider mechanism.

Since the sensor 616 of the above example provides the same output (e.g., binary output of "1" or "0") whenever its optical pathway is not blocked by the rib 610, a controller cannot determine the absolute position of the sliding panel 604 from the output of the sensor 616 alone. Thus, the controller may perform an initialization procedure to move the sliding panel 604 to a predetermined position and then track the position of the sliding panel 604 over time based on the number of open optical pathway detections by the sensor 616 when moving the sliding panel 604 in a given direction. An example of such a control method is illustrated in FIG. 14. Method 700 of FIG. 14 can be performed by a controller of a surgical light, such as controller 302 of FIG. 11.

Method 700 includes an initialization step 702 that may occur at power-up of the controller 302 (e.g., after a hard power cycle). The initialization step 702 may include controlling one or more actuators (e.g., actuator 306 of FIG. 11) to move the sliding panel 604 (the following description refers to a sliding panel 604 but it should be understood that this method is applicable to multiple sliding panels 604) to a desired initialized position. The initialized position could be, for example, a maximum travel position. The sliding panel 604 reaching the maximum travel position could be determined by the controller based on, for example, motor stall associated with the sliding panel 604 hitting a hard stop, the triggering of a limit switch, or through any other suitable mechanism. For example, the controller may control a motor of an actuator to rotate clockwise or counterclockwise until a motor stall is detected. Once this stall is detected, the controller "knows" that the sliding panel 604 is in the maximum travel position (e.g., all of the way to the left or all of the way to the right in FIG. 13A).

The controller may wait for a target spot size request at step 704, which may be received at step 706. A spot size request may be received at the controller from user interface 304 or user interface 312 of FIG. 11 based on a user input. If the target spot size is different from the spot size associated with the initialization position, a determination may be made at step 708 whether a motor should be moved in a predetermined direction (e.g., a clockwise direction). In the case of the sliding panel 604 being in the initialized position when reaching step 708, the determination at step 708 may always be associated with movement in the predetermined direction, since the sliding panel 604 may not be capable in moving in the other direction. However, if the position of the sliding panel 604 is at some other position than the initialized position, then the determination at step 708 will depend on what a current spot size is and what the target spot size is and will determine which direction the motor is controlled to turn and, thus, which direction the sliding panel 604 moves. For example, if a current spot size is "medium," which is associated with the sliding panel 604 being in a middle position (e.g., gap 622 aligned with sensor 616) and a target spot size is "large," then a determination at step 708 may be to rotate the motor clockwise, but if the target spot size is "small," then the determination at step 708 may be to rotate the motor counterclockwise.

If the determination at step 708 is that the motor should move in the predetermined direction, then at step 710, a determination is made of the number of detections by the sensor 616 (e.g., sensing by the sensor 616 the first end 618, second end 620, or gap 622 of the rib 610) needed for the sliding panel 604 to move to the position associated with the target spot size. For example, in the example of FIGS. 13A-C where there are three sliding panel positions, a target spot size that is one position away from the initialized position (e.g., a "medium" spot size position request, where the initialized position is a "large" spot size position) will result in a determination in step 710 of one detection by the sensor 616, and a target spot size that is two positions away from the initialized position (e.g., a "small" spot size position request, where the initialized position is a "large" spot size position) will result in a determination in step 710 of two detections by the sensor 616. A similar calculation is made at step 712 but, instead, associated with the sliding panel 604 moving in the opposite direction.

At step 714, the controller controls the motor to move in the desired direction until the number of detections by the sensor 616 that was determined in step 710 or 712 has been reached. Once the requisite number of rib openings has been detected, the controller may stop the motor at step 716 and update the slider position in a memory of the controller to the current position and return to step 704 to await a new target spot size request.

Figure 15:
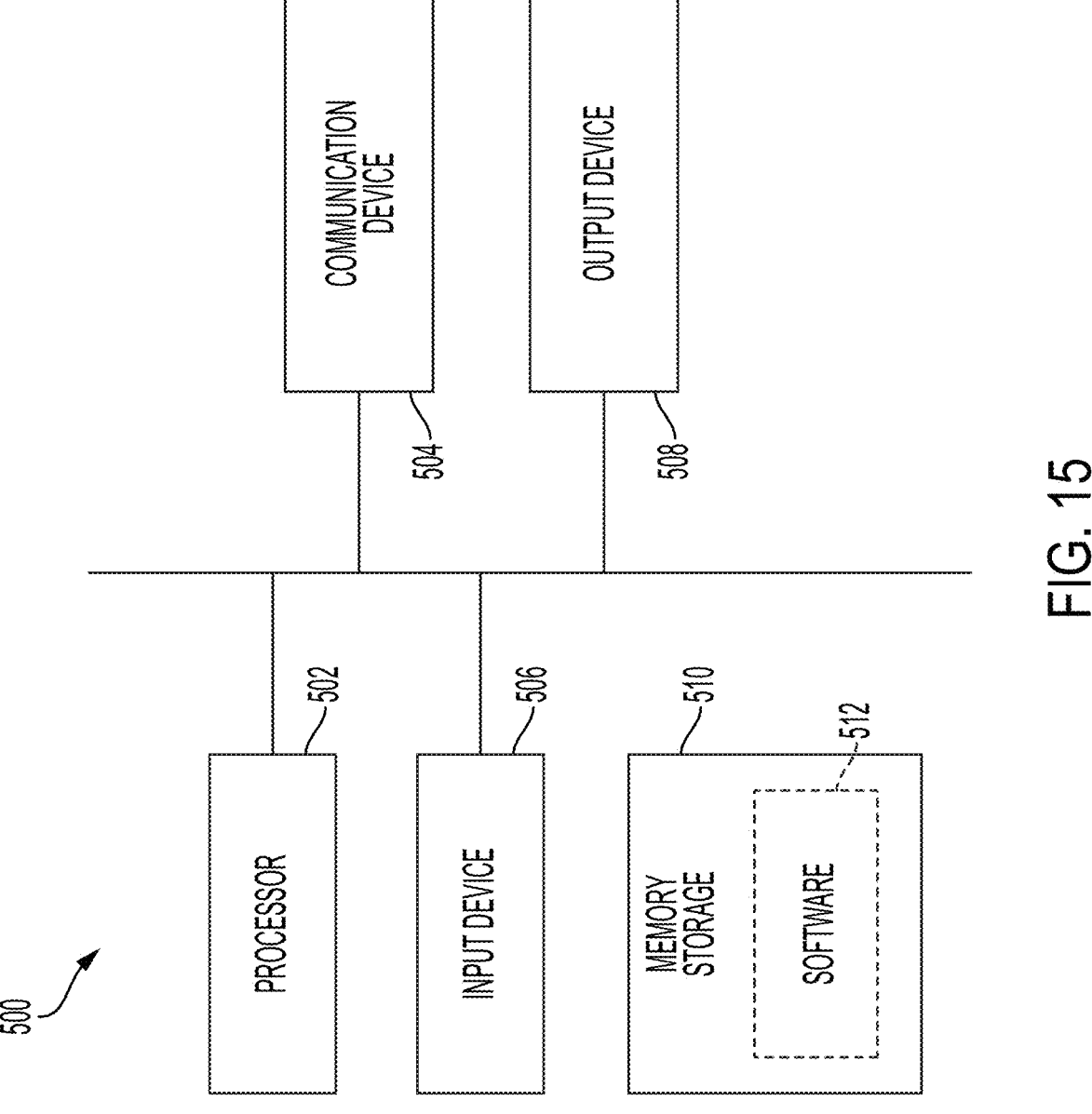
FIG. 15 shows an exemplary computing device, according to one or more examples of the disclosure.

FIG. 15 illustrates an exemplary computing device 500, in accordance with one or more examples of the disclosure. Device 500 can be a controller such as the controller 302 and/or the external controller 310 of FIG. 11. Device 500 can be a host computer connected to a network. Device 500 can be a client computer or a server. As shown in FIG. 13, device 500 can be any suitable type of microprocessor-based device, such as a personal computer, workstation, server, or handheld computing device (portable electronic device) such as a phone or tablet. The device can include, for example, one or more of processors 502, input device 506, output device 508, storage 510, and communication device 504. Input device 506 and output device 508 can generally correspond to those described above and can either be connectable or integrated with the computer.

Input device 506 can be any suitable device that provides input, such as a touch screen, keyboard or keypad, mouse, or voice-recognition device. Output device 508 can be any suitable device that provides output, such as a touch screen, haptics device, or speaker. The input device 506 can receive user inputs for adjusting spot size of light provided by a surgical light and may be located on a surgical light (e.g., user interface 14 on the surgical light 100 of FIG. 1), or externally from a surgical light (e.g., user interface 12 located remotely from the surgical light 100 of FIG. 1).

Storage 510 can be any suitable device that provides storage, such as an electrical, magnetic, or optical memory, including a RAM, cache, hard drive, or removable storage disk. Communication device 504 can include any suitable device capable of transmitting and receiving signals over a network, such as a network interface chip or device. The components of the computer can be connected in any suitable manner, such as via a physical bus or wirelessly.

Software 512, which can be stored in storage 510 and executed by processor 502, can include, for example, the programming that embodies the functionality of the present disclosure (e.g., as embodied in the devices as described above), such as for implementing one or more steps of process 400 of FIG. 12.

Software 512 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 510, that can contain or store programming for use by or in connection with an instruction execution system, apparatus, or device.

Software 512 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

Device 500 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 500 can implement any operating system suitable for operating on the network. Software 512 can be written in any suitable programming language, such as C, C++, Java, or Python. In various examples, application software embodying the functionality of the present disclosure can be deployed in different configurations, such as in a client/server arrangement or through a Web browser as a Web-based application or Web service, for example.

Accordingly, described herein is a surgical light that minimizes the weight and cost of the light that efficiently utilizes the light emitters of the surgical light by translating a focus panel with lenses that collimate and/or redirect light emitted from each light emitter to rely on the same number of light emitters to illuminate a small spot size and to illuminate a large spot size. The surgical light maintains both the parallelism of the focus panel relative to the light emitter and the alignment between the focus panel and the light emitters via alignment pins that permit the focus panel to move toward or away from the light emitters via tabs of the focus panel engaged with movable tracks driven by one or more actuators.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A surgical light comprising:
a housing;
a plurality of light emitters mounted to the housing and arranged in a plurality of subgroups;
a focus panel assembly mounted to the housing such that the focus panel assembly can translate relative to the housing, wherein the focus panel assembly can be translated in an axial direction toward and away from the plurality of light emitters, and wherein the focus panel assembly comprises a plurality of subgroups of lenses and each subgroup of lenses aligns to a corresponding subgroup of light emitters independently of other subgroups of lenses of the plurality of subgroups of lenses;
at least one track movably mounted to the housing and engaged by at least one tab of the focus panel assembly; and
at least one actuator for moving the at least one track such that the at least one tab of the focus panel assembly travels along the at least one track, thereby axially translating the focus panel assembly toward or away from the plurality of light emitters for adjusting a spot size of light provided by the surgical light at a target.

2. The surgical light of claim 1, wherein the housing comprises a plurality of alignment pins and the focus panel assembly is mounted to the housing such that the plurality of alignment pins prevent the focus panel assembly from rotating relative to the housing.

3. The surgical light of claim 1, wherein the at least one track is located centrally with respect to the focus panel assembly, and wherein a ring is rotatably mounted to the housing and the ring comprises the at least one track.

4. The surgical light of claim 1, wherein the at least one track is located at a periphery of the focus panel assembly.

5. The surgical light of claim 1, wherein the at least one track comprises a plurality of tracks.

6. The surgical light of claim 1, wherein the at least one track comprises at least one ramped portion for driving the focus panel assembly in the axial direction and at least one flat portion for retaining the focus panel assembly in an axial position.

7. The surgical light of claim 1, wherein the at least one track comprises a ramped portion for driving the focus panel assembly in the axial direction.

8. The surgical light of claim 1, wherein a sliding panel comprises the at least one track and a rack, the sliding panel movably mounted relative to the housing and engaged by the at least one tab of the focus panel assembly, and the at least one actuator comprises a pinion for driving the rack.

9. The surgical light of claim 8, wherein the at least one actuator comprises a ring-shaped rack that drives a rod to which the pinion is mounted, and wherein the ring-shaped rack drives a plurality of rods that drive a plurality of tracks.

10. The surgical light of claim 1, further comprising a controller that is communicably coupled to the at least one actuator, wherein the controller is configured to cause the at least one actuator to move the at least one track in response to receiving a command.

11. The surgical light of claim 10, wherein the command corresponds to a predefined focus setting and the at least one track is moved by a predefined amount associated with the predefined focus setting.

12. A method for adjusting a spot size of light provided by a surgical light at a target, the method comprising:
receiving a command at a controller of the surgical light to adjust the spot size of light; and
in response to receiving the command, moving at least one track movably mounted to a housing of the surgical light by at least one actuator such that at least one tab of a focus panel assembly of the surgical light travels along the at least one track, thereby axially translating the focus panel assembly in an axial direction toward or away from a plurality of light emitters mounted to the housing and arranged in a plurality of subgroups, wherein the focus panel assembly is mounted to the housing such that the focus panel assembly can translate relative to the housing, and wherein the focus panel assembly comprises a plurality of subgroups of lenses and each subgroup of lenses aligns to a corresponding subgroup of light emitters independently of other subgroups of lenses of the plurality of subgroups of lenses.

13. The method of claim 12, wherein the housing comprises a plurality of alignment pins and the focus panel assembly is mounted to the housing such that the plurality of alignment pins prevent the focus panel assembly from rotating relative to the housing.

14. The method of claim 12, wherein the command corresponds to a predefined focus setting and the at least one track is moved by a predefined amount associated with the predefined focus setting.

15. The method of claim 12, wherein the at least one track is located centrally with respect to the focus panel assembly, and wherein a ring is rotatably mounted to the housing and the ring comprises the at least one track.

16. The method of claim 12, wherein the at least one track is located at a periphery of the focus panel assembly.

17. The method of claim 12, wherein the at least one track comprises a plurality of tracks.

18. The method of claim 12, wherein the at least one track comprises at least one ramped portion and at least one flat portion, and moving the at least one track comprises:
driving the focus panel assembly in the axial direction via the at least one ramped portion; and
retaining the focus panel assembly in at least one axial position via the at least one flat portion.

19. The method of claim 12, wherein the at least one track comprises a ramped portion, and moving the at least one track comprises driving the focus panel assembly in the axial direction via the ramped portion.

* * * * *